(12) United States Patent
Chang et al.

(10) Patent No.: US 7,507,532 B2
(45) Date of Patent: Mar. 24, 2009

(54) CANCER SPECIFIC GENE MH15

(75) Inventors: Stanley Chang, Taipei (TW); Hsun-Lang Chang, Hualien (TW); Wei-Ying Kuo, Gueishan Township, Taoyuan County (TW); Kuo-Yen Chen, Banciao (TW); Ning-Yi Li, Taipei (TW); Chih-Ping Hsu, Jhudong Township, Hsinchu County (TW); Pei-Hsun Ho, Sinjhuang (TW)

(73) Assignee: Medigen Biotechnology Corporation, Taiwan (TW)

( * ) Notice: Subject to any disclaimer, the term of this patent is extended or adjusted under 35 U.S.C. 154(b) by 210 days.

(21) Appl. No.: 11/074,129

(22) Filed: Mar. 7, 2005

(65) Prior Publication Data

US 2006/0068411 A1    Mar. 30, 2006

Related U.S. Application Data

(60) Provisional application No. 60/551,084, filed on Mar. 8, 2004.

(51) Int. Cl.
*C12Q 1/68*   (2006.01)
(52) U.S. Cl. ............................................. 435/6
(58) Field of Classification Search .................. 435/6
See application file for complete search history.

(56) References Cited

U.S. PATENT DOCUMENTS

2002/0151681 A1 * 10/2002 Rosen et al. ................. 530/350

FOREIGN PATENT DOCUMENTS

WO     WO01/77385 A1     10/2001
WO     WO03/029421 A2     4/2003

OTHER PUBLICATIONS

Tockman et al (Cancer Res., 1992, 52:2711s-2718s).*
Tockman et al (Cancer Res., 1992, 52:2711s-2718s).*
Kariko et al (Journal of Immunology, Jun. 2004, 172(11):6545-6549).*
Scacheri et al (PNAS, Feb. 2004, 101(7):1892-1897).*
Tockman et al (Cancer Res., 1992, 52:2711s-2718s).*
MacDonald, John S., *Seminars in Oncology*, vol. 30, No. 4, Suppl 11, Aug. 2003, pp. 19-25.
Roukos, Dimitrios H., *Annals of Surgical Oncology*, 11(2): 127-129, Feb. 2004.
Tang, Wozhan et al., *Mammalian Genome* 8, 695-696 (1997).
Strausberg, Robert L., et al., *PNAS*, vol. 99, No. 26, Dec. 24, 2002, 16899-16903.
Biacore Life Sciences, www.biacore.com/lifesciences/index.html, Nov. 8, 2005.

* cited by examiner

*Primary Examiner*—Sean E Aeder
(74) *Attorney, Agent, or Firm*—Whyte Hirschboeck Dudek S.C.

(57) ABSTRACT

MH15 (Hn1L) is identified as an oncogene. Methods and compositions for detecting and diagnosing cancer in patients are provided, by determining the level of MH15 expression in biological samples. Also provided are methods for screening for inhibitors and moderators of MH15 expression and activity, as well as compositions comprising compounds and molecules that inhibit or moderate MH15 expression or activity, thereby treating cancer, in vivo.

5 Claims, 10 Drawing Sheets

FIG. 1

SEQ ID NO: 1 nucleotide sequence of MH15.

```
   1 GGCGCGCGGC GAGCTGAGGG TGGCGGCGGT CGACATGTTC CAGGTCCCGG ATAGCGAGGG
  61 CGGCCGCGCC GGCTCCAGGG CCATGAAGCC CCAGGAGGA GAATCGAGCA ATCTTTTGG
 121 AAGTCCAGAA GAAGCCACTC CTTCCAGCAG GCCTAATAGG ATGGCATCTA ATATTTTGG
 181 ACCAACAGAA GAACCTCAGA ACATACCCAA GAGGACAAAT CCCCCAGGGG GTAAAGGAAG
 241 TGGTATCTTT GACGAATCAA CCCCCGTGCA GACTCGACAG CACCTGAACC CACCTGGAGG
 301 GAAGACCAGC GACATTTTTG GGTCTCCGGT CACTGCCACT TCACGCTTGG CACACCCAAA
 361 CAAACCCAAG GATCATGTTT TCTTATGTGA AGGAGAAGAA CCAAAATCGG ATCTTAAAGC
 421 TGCAAGGAGC ATCCCGGCTG GAGCAGAGCC AGGTGAGAAA GGCAGCGCCA GAAAAGCAGG
 481 CCCCGCCAAG GAGCAGGAGC CCATGCCCAC AGTCGACAGC CATGAGCCCC GGCTGGGGCC
 541 GCGGCCTCGC TCTCACAACA AGGTCCTGAA CCCACCGGGA GGCAAATCCA GCATCTCCTT
 601 CTACTAAGAG AAGCCACTGC TCCACCCGGA GCCAGACCAG AAACTCAAGA GATAGGGTAG
 661 CCATGTTTTC ATTTCCTTTT GCCCAAATGA GCGGGGTGGG AAGAGGGTTA GTCTTATGTG
 721 AGCCTGGCTG CTCAGCGTCT CCTGGCCGTC ATGACAGCTG CTTGGAGACC CGTGCCTTCC
 781 AGATGGCTGG GAGATGCCTC TGTGGGGATG AAATGGGGCA CCCCTGGCCA TCACTCATGT
 841 GTAGTCCAGG TTTGAGAGGA ACTGGAAGGG GGGTGAGGGT GGGGAGGTGG GGCAGGGCAT
 901 GGTCCTTGGA TCAACAGCCC GCCAGCTGAT TGGATGTCTA GGAATGACTG AAAGAAACCA
 961 AAACAGCCTG TCCACTGCTG CTGTGGGATG GAGGAGGCGT AAGCAGAAAC ACTAACAGTA
1021 TATTGACCTC TTAGCAGAAC CGCTTCCATT CTGGAGATCA CGGCTGCTAA ATCCAGCATC
1081 CCCACTTCAT TTTACCCCCA GCATATTGTT CTGTAGTCTT TTCTTGAAAC ATCTTGATTG
1141 CTTTTCCTCG GCAGCTTTCA AAAAACCAAA TAATAATAGT TATCCGTCTT CTACTTCATG
1201 GAAGATTGTT TTGGTGCCCT GACCCTCTGA AGTGCCCAGT TCCTGCCATC TGAAACCTCG
1261 GCCTGATCTG ATCTCATGTT GGAATCTGCC TGTCTTTCAC ACAGGGCTGG TCTTGGTCCT
1321 TTACATGCCA GTTTTGCTTG TGAATTCTTG CTTTTTTCCT CTCATCAGCC TTAAGTTTAG
1381 GCGTTTGTTG TTCTCCAGTG ATGTAGACAG TTCCCTTCAC AAGTCACAGT TCTTCCCATA
1441 AATGAGGCCC GCTGACCTCT GCGGGACTTT AAAAATCTAT TCAGATATTT CCGAGTAAGT
1501 GGCTTGTTTA AATTCTTCCT GTGTCTTTCT TTATTCCTTA ATTGGTTGGT GGAAAGAAGA
1561 GATGCTTGGG AACCTTGGGT TCTTAGGTTT GGATTCTTTA ATAATATCTA AAAAGCTAAA
1621 TTTTAAATAC CAGCTTTACA TAAATGATTG TTGACTCTGG TCTGTTTCTG ACACCTTTCC
1681 AGAAAAAAGT CAATTGTTCA GGTACACCAA AGAGGAAGAA GAGCTGTGGA GGCCACCCTC
1741 TACAAAGCTT TATAGAACTT CTGGATCTAA CTCACAAACA AGCTTCCAGA AGAGACTAGA
1801 GACCTTAGGC CAGGAGATGA AGGAGTTCAG TAGCAAAGTC ACACCTGTCC AATTCCTGA
1861 GCTTTGCTCA CTCAGCTAAT GGGATGGCAA AGGTGGTGGT GCTTTCATCT TCAGGCAGAA
1921 GCCTCTGCCC ATCCCCCTCA AGGGCTGCAG GCCCAGTTCT CATGCTGCCC TTGGGTGGGC
1981 ATCTGTTAAC AGAGGAGAAC GTCTGGGTGG CGGCAGCAGC TTTGCTCTGA GTGCCTACAA
2041 AGCTAATGCT TGGTGCTAGA AACATCATCA TTATTAAACT TCAGAAAAGC AGCAGCCATG
2101 TTCAGTCAGG CTCATGCTGC CTCACTGCTT AAGTGCCTGC AGGAGCCGCC TGCCAAGCTC
2161 CCCTTCCTAC ACCTGGCACA CTGGGGTCTG CACAAGGCTT TGTCAACCAA AGACAGCTTC
2221 CCCCTTTTGA TTGCCTGTAG ACTTTGGAGC CAAGAAACAC TCTGTGTGAC TCTACACACA
2281 CTTCAGGTGG TTTGTGCTTC AAAGTCATTG ATGCAACTTG AAAGGAAACA GTTTAATGGT
2341 GGAAATGAAC TACCATTTAT AACTTCTGTT TTTTTATTGA GAAATGATT CACGAATTCC
2401 AAATCAGATT GCCAGGAAGA AATAGGACGT GACGGTACTG GGCCCTGTGA TTCTCCCAGC
2461 CCTTGCAGTC CGCTAGGTGA GAGGAAAAGC TCTTTACTTC CGCCCCTGGC AGGGACTTCT
2521 GGGTTATGGG AGAAACCAGA GATGGGAATG AGGAAAATAT GAACTACAGC AGAAGCCCCT
2581 GGGCAGCTGT GATGGAGCCC CTGACATTAC TCTTCTTGCA TCTGTCCTGC CTTCTTTCCC
2641 TCTGCGAGGC AGTGGGGTGG GATTCAGAGT GCTTAGTCTG CTCACTGGGA AGAAGAGT
2701 TCCTGCGCAT GCAAGCCCTG CTGTGTGGCT GTCGTTTACA TTTGGGAGGT GTCCTGTATG
2761 TCTGTACGTT GGGGACTGCC TGTATTTGGA AGATTTAAAA ACCTAGCATC CTGTTCTCAC
2821 CCTCTAAGCT GCATTGAGAA ATGACTCGTC TCTGTATTTG TATTAAGCCT TAACACTTTT
2881 CTTAAGTGCA TTCGGTGCCA ACATTTTTTA GAGCTGTACC AAAACAAAAA GCCTGTACTC
2941 ACATCACAAT GTCATTTTGA TAGGAGCGTT TTGTTATTTT TACAAGGCAG AATGGGGTGT
3001 AACAGTTGAA TTAAACTAGC AATCACGTGC TCAGAGCTTT
```

SEQ ID NO: 2 deduced protein sequence of MH15.

```
  1  MFQVPDSEGG  RAGSRAMKPP  GGESSNLFGS  PEEATPSSRP  NRMASNIFGP   50
 51  TEEPQNIPKR  TNPPGGKGSG  IFDESTPVQT  RQHLNPPGGK  TSDIFGSPVT  100
101  ATSRLAHPNK  PKDHVFLCEG  EEPKSDLKAA  RSIPAGAEPG  EKGSARKAGP  150
151  AKEQEPMPTV  DSHEPRLGPR  PRSHNKVLNP  PGGKSSISFY              190
```

FIG. 3
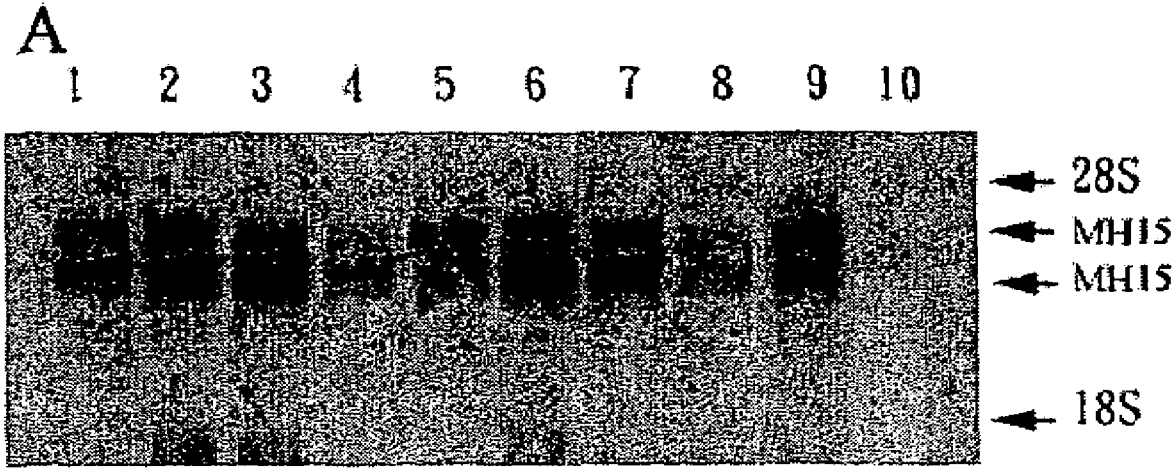
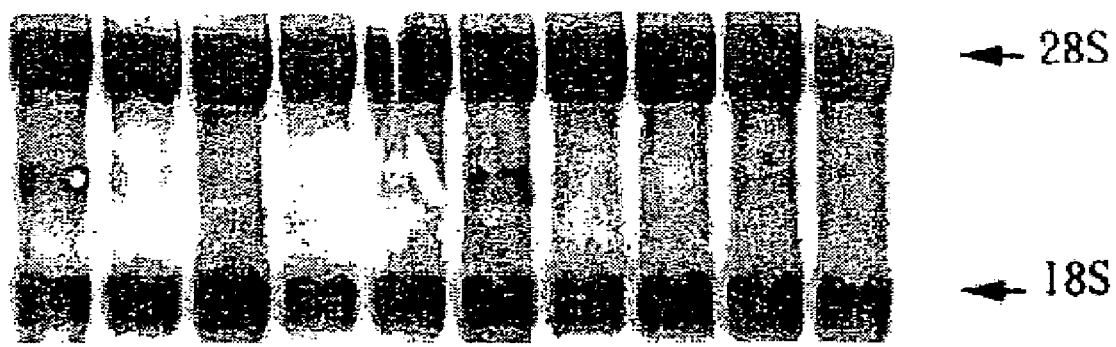

FIG. 5
A. NIH-3T3
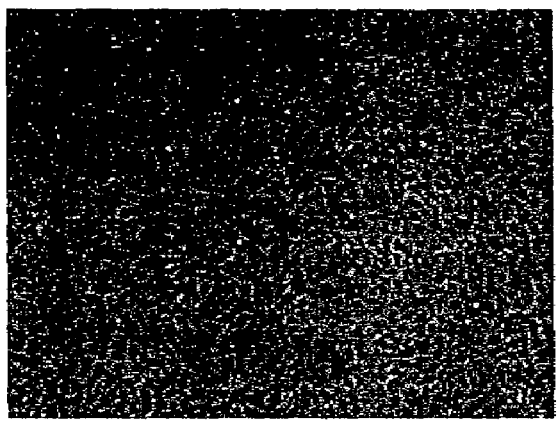
B. Vector
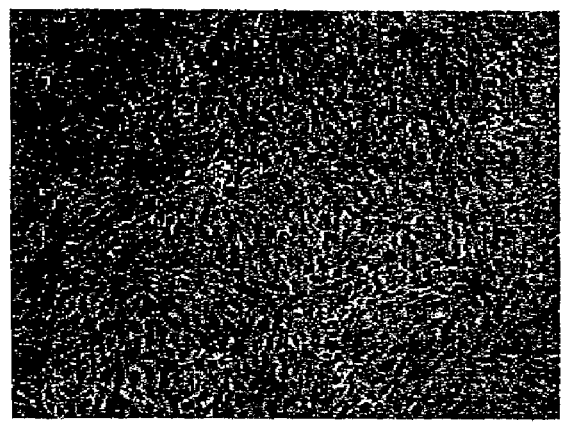
C. MH15-4
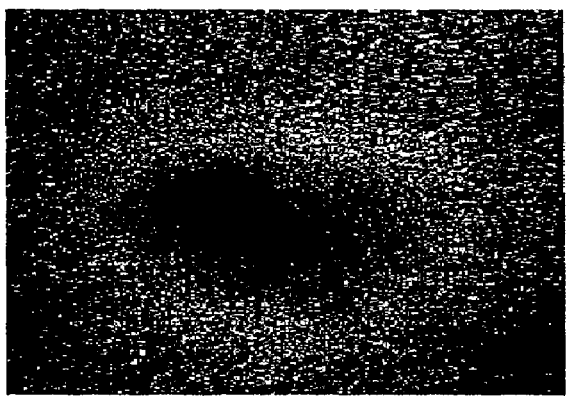
D. MH15-11
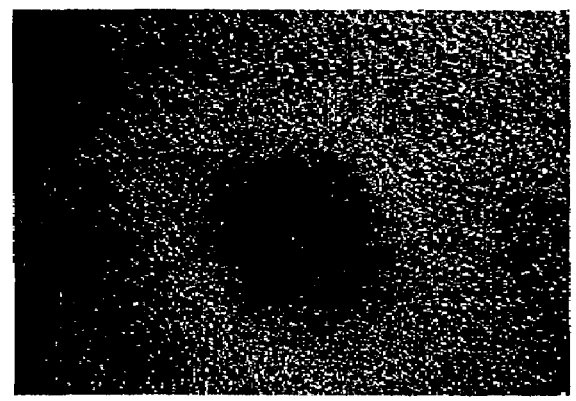

Fig 7
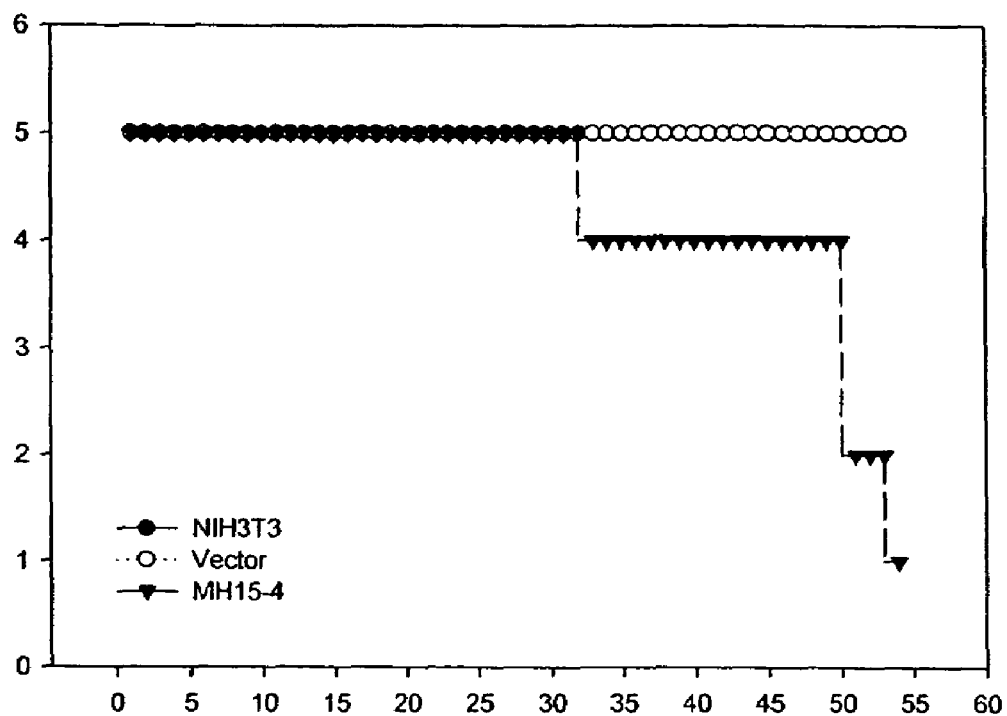
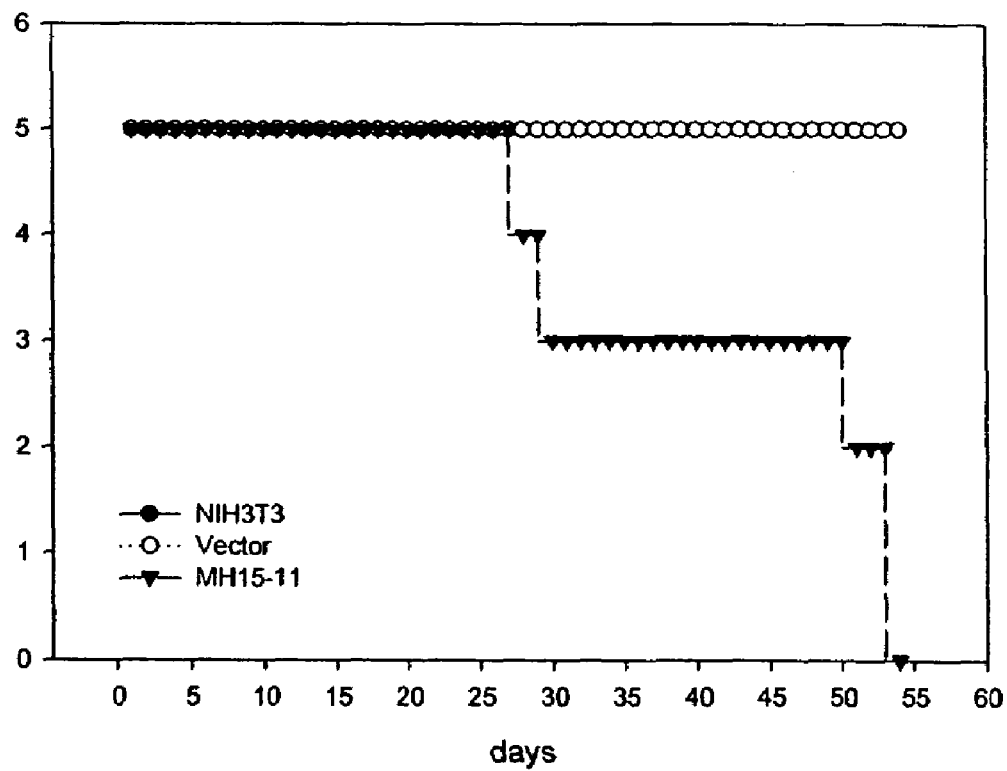

Fig 9
A
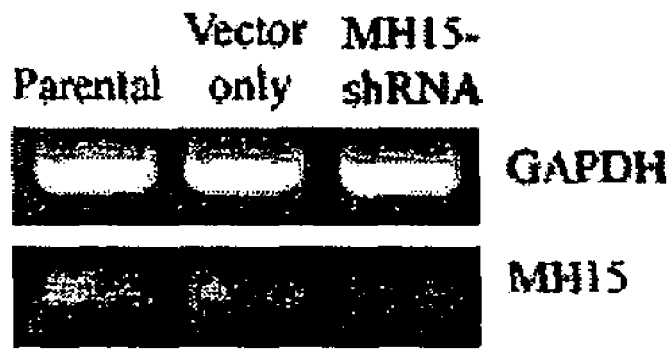
B
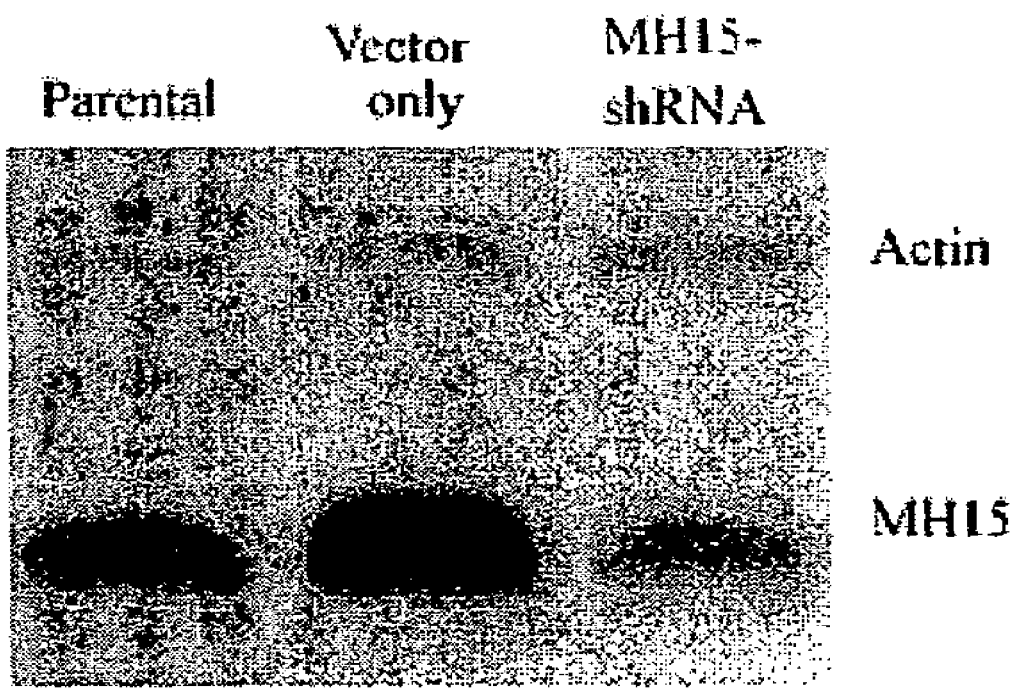

CANCER SPECIFIC GENE MH15

CROSS REFERENCE TO RELATED APPLICATION

This application claims the benefit of U.S. provisional application Ser. No. 60/551,084 filed on Mar. 8, 2004, pending.

BACKGROUND OF THE INVENTION

Cancer is the uncontrolled growth and spread of cells that may affect almost any tissue of the body. Lung, colorectal and stomach (gastric) cancer are among the five most common cancers in the world for both men and women. In the United States up to one third of the population develop cancer during their life span. As a result, in the USA alone it is estimated that about 500,000 individuals die from cancer annually (Ahmedin et al., CA Cancer J. Clin. 52:23-47 (2002)).

With global improvements in public health provision, populations are increasingly living to a greater age. The World Health Organisation estimates that more than 10 million people are diagnosed with cancer every year. It is further estimated that there will be 15 million new cases every year by 2020. In fact, cancer causes 6 million deaths every year-or 12% of deaths worldwide.

Turning to the biological perspective, as a normal cell progresses through the complex process of transformation to reach a cancerous, or 'neoplastic', state, its gene expression profile can typically change. Expression of certain genes that are usually dormant in a normal healthy cell may be turned on or up regulated in a cancer cell. Likewise, genes that maintain a normal healthy phenotype can be switched off or suppressed in cancer cells. Consequently, such genes can be viewed as biomarkers of neoplastic behavior in cells. In some circumstances the cell itself might not yet have even transformed into a cancerous cell, but may only be predisposed to such a change in future.

Previously, identification of cancers—for example gastric cancer—has relied upon traditional methods of diagnosis. For instance, detection of tumors in the stomach and esophagus is usually achieved by radiography, following ingestion of a 'barium meal'. This results in potentially harmful exposure of the patient to X-rays. Hence, a less invasive method of tumor diagnosis, such as via blood or urine analysis is desirable.

Public awareness campaigns alerting individuals to the possible warning signs of cancer can have an impact on diagnosis and treatment of the disease. Large-scale cancer screening of otherwise healthy populations has also proven successful in some instances. Screening refers to the use of simple tests across a healthy population in order to identify individuals who have disease, but do not yet have symptoms. Examples include breast cancer screening using mammography and cervical cancer screening using cytology screening methods, including Pap smears. In order for screening to be successful it must be relatively simple to perform and consistently reliable.

However, there are currently very few large-scale screening programmes for cancers other than breast and cervical cancers. As a result, in many cases the disease can remain symptomatically undetectable in the patient until a very advanced stage. Hence, there is a need to identify novel markers of the presence of cancer and also the progression of the disease once it has become established in a patient. In particular, there is a need to identify novel genetic markers of the cancer that can be suitable candidates for inclusion in large scale screening programmes. In addition, there is a need to identify genes that are involved in the development and progression of cancer so that therapies can be designed accordingly.

The present invention relates to the identification of a novel marker for cancer called MH15. Expression of the MH15 gene is detectable in the blood of patients and the level of expression of the gene is correlated to the presence of cancer, particularly gastric cancer; breast cancer; pancreatic cancer; prostate cancer; uterine cancer; ovarian cancer; colon cancer; esophagus cancer; testicular cancer and lung cancer. The invention also provides methods and compositions for treating cancer, particularly gastric cancer; breast cancer; pancreatic cancer; prostate cancer; uterine cancer; ovarian cancer; colon cancer; esophagus cancer; testicular cancer and lung cancer.

These and other uses, features and advantages of the invention should be apparent to those skilled in the art from the teachings provided herein.

SUMMARY OF THE INVENTION

In a first aspect, the invention provides a method of detecting and diagnosing cancer in a patient in need thereof, comprising the steps of obtaining a biological sample from said patient and analysing said sample for expression of MH15. In one embodiment, expression of MH15 at a level in excess of a normal level is indicative of the presence of cancer. In a further embodiment, the sample comprises cells obtained from a biological source selected from: tissues; whole blood; serum; plasma; saliva; cerebrospinal fluid; ascites fluid; pleural fluid and urine. Alternatively, the cells may be obtained from a biopsy of a suspected tumor. In a specific embodiment the sample comprises peripheral blood mononuclear cells (PBMCs).

One embodiment of the invention provides for a method of detecting and diagnosing cancers selected from: gastric cancer; breast cancer; pancreatic cancer; prostate cancer; uterine cancer; ovarian cancer; colon cancer; esophagus cancer; testicular cancer and lung cancer.

In a second aspect the invention provides a method of detection and diagnosis of cancer in a patient comprising the steps of:
  (a) providing a biological sample from a subject;
  (b) detecting the level of MH15 in the biological sample; and
  (c) comparing the level of MH15, in the biological sample with that in a control sample obtained from a healthy individual;

wherein an increased level of MH15, in the biological sample compared to that in the control sample indicates the presence of neoplasm in the subject. The level of MH15 can be the polynucleotide level or a portion, fragment, variant or complementary strand thereof, mRNA level, cDNA level, polypeptide level or a portion or fragment thereof, protein level or a level of biological activity of MH15.

In a third aspect the invention provides a diagnostic kit suitable for detecting and diagnosing cancer in a patient in need thereof, comprising at least one nucleic acid probe that consists of a nucleotide sequence that is substantially complimentary to at least 15 contiguous bases of SEQ ID NO:1. In an embodiment of the invention the nucleic acid probe is immobilised on a surface, for example, optionally as part of a microarray.

In a fourth aspect the invention provides a diagnostic kit suitable for diagnosing cancer in a patient in need thereof, comprising at least one antibody, said antibody being capable of specifically binding to an MH15 polypeptide.

A fifth aspect of the invention provides for an in vitro method for monitoring the progression of cancer in a patient comprising the steps of:

(a) interacting a biological sample from a patient with a substance selected from polynucleotides, probes, primers, or a portion, fragment, variant or complementary strand thereof; or polypeptides, antibodies that interact with MH15, or a portion or fragment thereof;

(b) detecting the level of MH15 polynucleotide or polypeptide, or the portion, fragment, variant or complementary strand thereof, that interacts with the substance in the sample;

(c) repeating steps (a) and (b) using a biological sample from the patient at a subsequent point of time; and (d) comparing the level detected in step (c) with that in step (b) and there from monitoring the progression of the cancer in the patient.

In an embodiment of the invention, the method can be expanded to comprise the further steps of obtaining a plurality of biological samples from said patient at a plurality of time intervals in a time course, and comparing the expression of MH15 in each biological sample, thereby effecting a diagnosis of tumor progression in said patient over the entire course of the disease.

In a further aspect of the invention the method of the second and third aspects can be employed for monitoring patients for the recurrence of cancer, for example after a period of remission. A related aspect of the invention provides for a method of the second and fifth aspects of the invention for determining the prognosis of cancer in a patient. In this aspect, determination of MH15 expression levels allows the determination of the progress and likely outcome of cancer and cancer related diseases in a patient suffering from cancer.

In a further aspect of the invention the method of the fifth aspect can be employed for monitoring patients for the recurrence of cancer, for example after a period of remission. A related aspect of the invention provides for a method of the fifth aspect of the invention for determining the prognosis of cancer in a patient. In this aspect, determination of MH15 expression levels allows the determination of the progress and likely outcome of cancer and cancer related diseases in a patient suffering from cancer.

The invention may also provide for a nucleic acid probe comprising a nucleic acid sequence that is substantially complimentary to at least 12 contiguous bases of SEQ ID NO: 1. An embodiment of the invention provides nucleic acid probes that are oligonucleotide primers selected from any one of SEQ ID NOS:5-8, although the skilled person will appreciate that other primers/probes may be suitably designed according to methods known in the art.

A further aspect of the invention provides a polynucleotide vector comprising an isolated nucleic acid sequence that is substantially complimentary to at least 12, more preferably 15 and most preferably 18 contiguous nucleotides of a nucleic acid molecule of SEQ ID NO:1, a transcription promoter, and a transcription terminator. In the vector, the promoter is operably linked to the nucleic acid sequence that is substantially complimentary to a nucleic acid molecule of SEQ ID NO:1, and the isolated nucleic acid sequence that is substantially complimentary to a nucleic acid molecule of SEQ ID NO:1 is operably linked with the transcription terminator. In embodiments of the invention the vector may be a viral vector or a plasmid vector, or any other suitable vector known to a person of skill in the art. The vector of the invention is optionally an expression vector or a vector that is capable of generating short interfering double stranded RNAs (RNAi) in a transfected cell.

One aspect of the invention provides a mammalian cell comprising the aforementioned polynucleotide vector.

A further aspect of the invention provides for an expression vector comprising an isolated nucleic acid molecule of SEQ ID NO:1, a transcription promoter, and a transcription terminator, wherein the promoter is operably linked with the nucleic acid molecule of SEQ ID NO:1, and wherein the nucleic acid molecule of SEQ ID NO:1 is operably linked with the transcription terminator.

In a further aspect the invention provides a recombinant host cell comprising the expression vector, wherein the host cell is selected from bacterium; yeast; fungal cells; insect cells; mammalian cells; and plant cells.

Another aspect of the invention provides a method of producing an MH15 polypeptide, the method comprising culturing recombinant host cells that comprise the aformentioned expression vector, and that produce said polypeptide, and isolating said polypeptide.

In a further aspect of the invention, there is provided an antibody or antibody fragment that specifically binds to a polypeptide of SEQ ID NO: 2. In specific embodiments of the invention the antibody is suitably selected from: a polyclonal antibody; a murine monoclonal antibody; a humanized monoclonal antibody derived from a murine monoclonal antibody; a human monoclonal antibody; and an $f_{ab}$ antibody fragment. A further embodiment includes an anti-idiotypic antibody that specifically binds to the antibody or antibody fragment that binds to the polypeptide of SEQ ID NO: 2.

An additional aspect of the invention provides a method for inhibiting malignancy in cancer cells, the method comprising exposing said cancer cells to an inhibitor of MH15. Embodiments of the invention provide that the inhibitor of MH15 may suitably comprise a moiety selected from: a polynucleotide sequence that is substantially complimentary to the sequence of SEQ ID NO: 1; an oligonucleotide sequence that is substantially complimentary to at least 12 contiguous bases of SEQ ID NO:1; an oligonucleotide RNAi sequence that is substantially complimentary to at least 18 contiguous bases of SEQ ID NO:1; an antibody or antibody fragment as previously described; a small molecule; a glycoprotein; and a polysaccharide. In specific embodiments of the invention the tumor cells are either located in-vitro or in-vivo. In further embodiments of the invention, the inhibitor can be administered to the tumor cells in the form of liposomal suspension, or optionally by direct injection to the site of the tumor. In a preferred embodiment of the invention the inhibitor inhibits metastasis in a tumor.

A further aspect of the invention provides a pharmaceutical composition for the prevention, treatment and/or therapy of cancer in a patient, comprising an inhibitor of MH15 and a pharmaceutically acceptable carrier, wherein said inhibitor of MH15 comprises a moiety selected from: a polynucleotide sequence that is substantially complimentary to the sequence of SEQ ID NO: 1; an oligonucleotide sequence that is substantially complimentary to at least 12 contiguous bases of SEQ ID NO:1; an oligonucleotide RNAi sequence that is substantially complimentary to at least 18 contiguous bases of SEQ ID NO:1; an antibody as described previously; a small molecule; a glycoprotein; a polysaccharide and a pharmaceutically acceptable excipient and carrier.

Another aspect of the invention provides a vaccine composition, comprising a polynucleotide of SEQ ID NO:1 or polypeptide of SEQ ID NO:2, or an antigenic fragment of said polypeptide, and a pharmaceutically acceptable carrier. One embodiment of the invention provides the option of further adding a non-specific immune response adjuvant to the vaccine composition.

In a further aspect, the invention provides a vaccine composition, comprising the aforementioned expression vector, and a pharmaceutically acceptable carrier. One embodiment of the invention provides the option of also adding a non-specific immune response adjuvant to this particular vaccine composition.

Other aspects of the invention also provide methods of treating cancer in a patient in need thereof, comprising administering effective amounts of the pharmaceutical or vaccine compositions described to said patient.

A further aspect of the invention provides a method for identifying a molecule that interacts with MH15 comprising the steps of:
 a) screening a plurality of candidate molecules in order to identify one or more target molecules that bind to MH15 polypeptide;
 b) determining whether said one or more target molecules interacts with MH15 polypeptide so as to moderate MH15 biological activity; and
 c) characterising a target molecule that moderates MH15 biological activity as an MH15 interacting molecule.

In a preferred embodiment of the invention the method comprises the additional step of further characterising the MH15 interacting molecule for pharmaceutical compatibility. In specific embodiments of the invention the MH15 interacting molecule can be either an inhibitor of MH15 biological activity, or an enhancer of MH15 biological activity. It is preferred that the MH15 interacting molecule is selected from a protein; a peptide or a small molecule. In a specific embodiment of the invention the MH15 protein in part (a) is immobilised on a solid substrate such as a biochip, and optionally the method is performed using a BIAcore®.

A further aspect of the invention provides a method for identifying a molecule that moderates the expression of MH15 in a cell comprising:
 a) exposing a cell that expresses MH15 to a candidate molecule in order to identify whether said candidate molecule has a moderating effect on the expression of MH15 in the cell;
 b) determining whether said candidate molecule moderates MH15 expression levels; and
 c) characterising a candidate molecule that selectively moderates MH15 expression levels in the cell as an MH15 moderator molecule.

For all aspects an embodiments of the present invention, the polynucleotide can comprise a polynucleotide that has at least 50%, 60%, 70%, 80%, 90%, 95% or 99% complete sequence identity to MH15 as shown in SEQ ID NO: 1. Likewise, the polypeptide can comprise a polypolypeptide that has at least 50%, 60%, 70%, 80%, 90%, 95% or 99% complete sequence identity to MH15 as shown in SEQ ID NO: 2. Sequence identity can also be to a fragment or portion of the full-length polynucleotide or polypeptide. Hence, a sequence may have only 50% overall sequence identity with a sequence of the invention but in a particular region, domain or subunit could share 80%, 90%, or as much as 99% sequence identity with sequence of the invention.

According to the present invention, homology to the nucleic acid sequence of SEQ ID NO: 1 is not limited simply to sequence identity. Many nucleic acid sequences can demonstrate biologically significant homology to each other despite having apparently low sequence identity. In the present invention homologous nucleic acid sequences are considered to be those that will hybridise to each other under conditions of low stringency (Sambrook J. et al, Molecular Cloning: a Laboratory Manual, Cold Spring Harbor Press, Cold Spring Harbor, N.Y.).

BRIEF DESCRIPTION OF THE DRAWINGS

FIG. 1 shows both the full length DNA (SEQ ID NO: 1) and deduced protein sequence (SEQ ID NO: 2) of MH15.

FIG. 3A shows the Northern blot result of MH15 expression levels in the PBMC sample and cancer cell lines.

FIG. 3B shows the Northern blot result of 18S and 28S RNA in the PBMC sample and cancer cell lines.

FIG. 5 shows the morphological transformation caused by MH15 over-expression in NIH 3T3 cells.

FIG. 7 shows reduced survivability induced through metastasis by MH15 transfectants.

FIG. 9A shows the reduction of MH15 RNA levels in TOV112D ovarian cancer cells transfected with MH15 targeting shRNA.

FIG. 9B shows the reduction of MHL5 protein levels in TOV112D ovarian cancer cells transfected with MH15 targeting shRNA.

Figure 2:
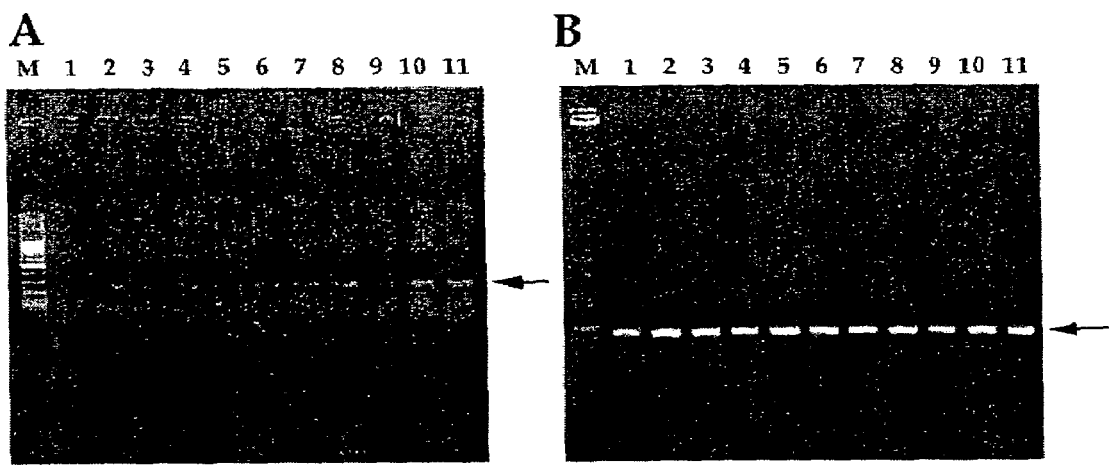
FIG. 2A shows the RT-PCR result of MH15 expression levels in the peripheral blood mononuclear cell (PBMC) sample and cancer cell lines.
FIG. 2B shows the RT-PCR result of GAPDH expression levels in the PBMC sample and cancer cell lines.

TAB. I shows the quantification for RT-PCR result of MH15 expression level in the peripheral blood mononuclear cell (PBMC) between gastric cancer patients and healthy volunteers.

TAB. II shows the quantification for real time-PCR result of MH15 expression level in the peripheral blood mononuclear cell (PBMC) between gastric cancer patients and healthy volunteers.

TAB. III shows the transforming properties of MH15 transfected NIH 3T3 cells.

TAB. IV shows the quantification for RT-PCR and western blotting of MH15 expression levels in TOV112D parental cell, vector only and MH15-shRNA transfectant.

DETAILED DESCRIPTION OF THE INVENTION

Prior to setting forth the invention, a number of definitions are provided that will assist in the understanding of the invention.

The term "allelic variant" is used herein to denote any two or more alternative forms of a gene occupying the same chromosomal locus and controlling the same inherited characteristic. Allelic variation arises naturally though mutation, and may result in phenotypic polymorphism within populations. Gene mutations typically result in an altered nucleic acid sequence and in some cases an altered polypeptide sequence also. As used herein, the term "allelic variant" is additionally used to refer to the protein or polypeptide encoded by the allelic variant of a gene.

An "antibody" denotes a protein that is produced in response to an antigen that is able to combine with and bind to the antigen, preferably at a specific site on the antigen, known as an epitope. The term as used herein includes antibodies of polyclonal and monoclonal origin, unless stated otherwise. Polyclonal antibodies are a group of antibodies produced by different B lymphocytes in response to the same antigen; different antibodies in the group typically recognize different parts (epitopes) on the antigen. A monoclonal antibody recognizes only one type of antigen and is produced by the daughter cells of a single antibody-producing lymphocyte, typically a hybridoma. Also included within the term 'antibody' are fragments, such as the Fab, F(ab')$_2$ and Fc portions, as well as derivatives of antibodies, such as chimeric fusions with labelling moieties including green fluorescent protein (GFP).

An "antigen" denotes a molecule that triggers an immune response. An antigen may be in the form of a full length polypeptide or protein. Alternatively, the antigen can be in the form of peptide fragments that bear the specific epitopes that allow antibodies raised against such fragments to also bind to the full length polypeptide.

The term "cancer" is used herein to denote a tissue or a cell located within a neoplasm or with properties associated with a neoplasm. Neoplasms typically possess characteristics that differentiate them from normal tissue and normal cells. Among such characteristics are included, but not limited to: a degree of anaplasia, changes in cell morphology, irregularity of shape, reduced cell adhesiveness, the ability to metastasize, increased levels of angiogenesis, increased cell invasiveness, reduced levels of cellular apoptosis and generally increased cell malignancy. Terms pertaining to and often synonymous with "cancer" include sarcoma, carcinoma, tumor, epithelioma, leukaemia, lymphoma, polyp, transformation, neoplasm and the like.

The term "complements of a polyncleotide molecule" denotes a polynucleotide molecule having a complementary base sequence and reverse orientation as compared to a reference sequence.

The term "expression vector" is used to denote a DNA molecule that is either linear or circular, into which another DNA sequence fragment of appropriate size can be integrated. Such DNA fragment(s) can include additional segments that provide for transcription of a gene encoded by the DNA sequence fragment. The additional segments can include and are not limited to: promoters, transcription terminators, enhancers, internal ribosome entry sites, untranslated regions, polyadenylation signals, selectable markers, origins of replication and such like. Expression vectors are often derived from plasmids, cosmids, viral vectors and yeast artificial chromosomes; vectors are often recombinant molecules containing DNA sequences from several sources.

The term "detection", as used herein is intended to encompass both direct and indirect detection of neoplasms or cancer. Direct detection of neoplastic cells, as the term implies, involves the identification of the presence of neoplastic cells and/or tissue in the patient or in tissue that has been removed from the patient and analysed in vitro, such as via biopsy. Indirect detection of neoplastic cells can consist of the identification of phenotypic signals, expression patterns, morphological changes or other signals that are correlated with or indicative of the presence of neoplastic cells in a patient or in tissue that has been removed from the patient and analysed in vitro. Suitable methods for detection of neoplastic tissues and/or cancer are described in more detail below. It is appreciated by the skilled person that the type of information derived from the step of detection need not simply be either positive or negative, but can also be used to allow for further evaluation of the type of neoplasm identified. In this way there may also be diagnostic or prognostic aspects associated with the act of detection.

The term "diagnosis", as used herein can encompass both the acts of positively detecting disease, such as cancer, in a biological sample taken from a patient, as well as the step of correlating presence of disease in a sample to the likely presence of the disease in the patient. Hence, in accordance with the present invention an act of diagnosis can be detection of a disease pathology in a sample, correlation of such pathology with the presence of disease in a patient from which the sample was taken, or the combination of both the steps of detection and correlation.

The term "isolated", when applied to a polynucleotide sequence, denotes that the sequence has been removed from its natural organism of origin and is, thus, free of extraneous or unwanted coding or regulatory sequences. The isolated sequence is suitable for use in recombinant DNA processes and within genetically engineered protein synthesis systems. Such isolated sequences include cDNAs and genomic clones. The isolated sequences may be limited to a protein encoding sequence only, or can also include 5' and 3' regulatory sequences such as promoters and transcriptional terminators.

The term "isolated", when applied to a polypeptide is a polypeptide that has been removed from its natural organism of origin. It is preferred that the isolated polypeptide is substantially free of other polypeptides native to the proteome of the originating organism. It is most preferred that the isolated polypeptide be in a form that is at least 95% pure, more preferably greater than 99% pure. In the present context, the term "isolated" is intended to include the same polypeptide in alternative physical forms whether it is in the native form, denatured form, dimeric/multimeric, glycosylated, crystallised, or in derivatized forms.

As used herein, a "biological sample" refers to a cell or a population of cells or a quantity of tissues or body fluid, such as whole blood, serum, plasma, saliva, cerebrospinal fluid or urine from a subject or patient, wherein a quantity of tissues, e.g., blood tissues, removed from a human is more preferable. In contrast, a "control sample", as used herein, refers to a sample that corresponds to the biological sample described above, but which demonstrates normal levels of MH15 expression (i.e., not affected by neoplasms). The level or amount of MH15 can be measured based on quantitative or qualitative methods, as described in detail below.

The term "normal level" when in the context of levels of gene expression, is used herein to denote the level of gene expression in healthy non-diseased samples. Normal levels of expression represent the baseline or control level of expression of a gene. Aberrant expression levels in cells, either at levels that are too high or too low, are considered not to be normal and can be indicative of disease in the samples from which the cells have been obtained, e.g. cancer.

The term "operably linked", when applied to DNA sequences, for example in an expression vector, indicates that the sequences are arranged so that they function cooperatively in order to achieve their intended purposes, i.e. a promoter sequence allows for initiation of transcription that proceeds through a linked coding sequence as far as the termination sequence.

A "polynucleotide" is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Polynucleotides include DNA and RNA, and may be manufactured synthetically in vitro or isolated from natural sources. Sizes of polynucleotides are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 40 nucleotides in length are typically called "oligonucleotides".

A "polypeptide" is a polymer of amino acid residues joined by peptide bonds, whether produced naturally or in vitro by synthetic means. Polypeptide of less than approximately 12 amino acid residues in length is typically referred to as a "peptide". The term "polypeptide" as used herein denotes the product of a naturally occurring polypeptide, precursor form or proprotein. Polypeptides also undergo maturation or post-translational modification processes that may include, but are not limited to: glycosylation, proteolytic cleavage, lipidization, signal peptide cleavage, propeptide cleavage, phosphorylation, and such like. A "protein" is a macromolecule comprising one or more polypeptide chains.

The term "promoter" as used herein denotes a site on DNA to which RNA polymerase will bind and initiate transcription. Promoters are commonly, but not always, located in the 5' non-coding regions of genes.

All references cited herein are incorporated by reference in their entirety. Unless otherwise defined, all technical and scientific terms used herein have the same meaning as commonly understood by one of ordinary skill in the art to which this invention belongs.

The present invention is based in part upon the discovery that the MH15 gene is expressed at elevated levels in neoplasms and PBMCs of cancer patients.

As described in more detail below, elevated levels of MH15 expression in PBMCs is a detection and diagnostic indicator of cancer. This is of particular advantage as it allows for mass screening of populations for the presence of cancer by, for example, a simple blood test. The present invention, therefore, provides methods, apparatus and compositions for the prevention, detection, diagnosis and/or treatment of cancers in patients.

The MH15 gene is also known as Hn1L (Hn1-like, GEN-BANK accession no. BC060853) and is mapped to reside on human chromosome 16p13.3. It is a deduced 190-amino acid protein and designated as chromosome 16 open reading frame 34, with a calculated molecular mass of 20 KD. Another gene Hn1, however, is expressed in many fetal and adult tissues, with the highest levels in hematopoietic cells and fetal brain tissues. It was postulated that Hn1 is important in hemopoietic and neurological development. Though MH15 (Hn1L) shares approximately 30% identity with Hn1, to date no function has yet been proposed for Hn1L.

In the present invention, a striking correlation has been observed between MH15 gene expression and cancer. It is noted that the expression of MH15 is significantly different between healthy patients and cancer patients. More specifically, the expression of MH15 in the PBMCs is elevated in cancer patients compared to normal healthy individuals. As is evident from FIG. 2, MH15 expression is undetectable in PBMCs from healthy individuals. However, it can be seen in Tables I and II that MH15 expression is elevated to detectable levels in patients suffering from gastric cancer. Hence, MH15 represents an excellent biomarker for detection of cancer. Accordingly, it is believed that MH15 can play an important regulatory role in vivo and can function as an oncogene.

The present invention also relates to the discovery that the expression of MH15 in NIH3T3 fibroblasts can induce tumorigenesis and metastasis. In particular, the inventors have identified that tumors transformed by MH15 can readily metastasize to the liver and intestine. In addition, MH15 is also found to be over-expressed in several kinds of cancer tissues including gastric cancer; breast cancer; pancreatic cancer; prostate cancer; uterine cancer; ovarian cancer; colon cancer; esophagus cancer; testicular cancer and lung cancer. Hence, MH15 has been identified as an important therapeutic target for the treatment of cancer and, in particular, the inhibition of metastasis in patients with cancer.

Expression levels of MH15 can be determined via a number of techniques commonly known to the person of skill in the art. MH15 expression can be determined by looking at the level of MH15 mRNA in cells, or by detecting the amount of MH15 protein present in a biological sample.

Total RNA can be extracted from cells in a sample using standard single step RNA extraction procedures (Chomczynski P. and Sacchi N. Anal Biochem 1987; 162:156). Total RNA extraction reagents such as TRIzol® reagent are also suitable (Invitrogen, Life Technologies, Inc.)

Suitable methods for detection of MH15 mRNA in a sample from which RNA has been extracted, include but are not limited to: RT-PCR, RNase protection assay, and northern blot assay (Sambrook J. et al, Molecular Cloning: a Laboratory Manual, Cold Spring Harbor Press, Cold Spring Harbor, N.Y.). In addition, the probes may be immobilised on a substrate so as to form part of a microarray, that allows screening of the sample for many different biomarkers in addition to expression of MH15.

Suitable nucleic acid probes or oligonucleotide primers can be designed based upon the sequence of MH15 provided in SEQ ID NO:1. Those skilled in the art will recognize that the sequence disclosed in SEQ ID NO: 1 represents a single allele of human MH15 (Hn1L) and that allelic variation and alternative splicing are expected to occur. Detection of expression of allelic variants of the DNA sequence shown in SEQ ID NO:1, including those containing silent mutations and those in which mutations result in amino acid sequence changes, are within the scope of the present invention. Allelic variants of the sequence of SEQ ID NO:1 can be cloned by probing cDNA or genomic libraries from different individuals according to standard procedures.

The present invention also provides for detection and diagnosis of cancer from samples containing elevated levels of expression of mRNA and polypeptide that have substantially similar sequence identity or homology to that of SEQ ID NO: 1 or 2 respectively. The term "substantially similar sequence identity" is used herein to denote a level of sequence similarity of from about 50%, 60%, 70%, 80%, 90%, 95% to about 99% identity. Percent sequence identity can be determined using conventional methods (Henikoff and Henikoff Proc. Natl. Acad. Sci. USA 1992; 89:10915, and Altschul et al. Nucleic Acids Res. 1997; 25:3389-3402).

It is also within the scope of the invention for specific variants of the MH15 sequence defined in SEQ ID NO:1 to be diagnostic of the presence of different types of cancers in a patient.

Detection of the presence of neoplasms can be achieved by use of nucleic acid hybridization methods, such as Southern analysis, Northern analysis, or in situ hybridization, to identify the level of MH15 expression in a biological sample. The overexpression of the MH15 gene can be indicated by hybridization of the gene in mRNA or cDNA to a suitably designed nucleic acid probe (Sambrook J. et al, Molecular Cloning: a Laboratory Manual, Cold Spring Harbor Press, Cold Spring Harbor, N.Y.).

In accordance with the present invention RT-PCR, in which PCR is applied in conjunction with reverse transcription, has been successfully used. RT-PCR analysis may be performed on biological samples taken from a subject and on control samples taken from a healthy individual who is not afflicted with a neoplasm.

In yet another embodiment, assays of nucleic acid (e.g., oligonucleotide) probes that are complementary to target nucleic acid sequence segments from a subject, are used to identify the expression of MH15 genes. Optionally, an oligonucleotide array (microarray) can be used. Oligonucleotide arrays generally comprise a plurality of different oligonucleotide probes that are immobilized on a surface of a substrate in different known spots. The surface is typically biocompatible. These oligonucleotide arrays, also called "DNA chips" or "biochips", have been generally disclosed in the art, for example, U.S. Pat. Nos. 6,605,363, 6,528,291, 6,403,368, and 6,350,620.

MH15 protein expression can be analysed in-situ within the sample or in extracts of protein made from the sample. Standard techniques for protein detection include western blotting, antibody staining, and ELISA (Sambrook J. et al, Molecular Cloning: a Laboratory Manual, Cold Spring Harbor Press, Cold Spring Harbor, N.Y.). Detection of MH15 protein in either native or denatured form can be made using polyclonal antibodies prepared according to standard techniques. Alternatively, monoclonal antibodies to MH15 polypeptide can be prepared (Galfre G. and Milstein C. Methods Enzymol. 1981; 73(Pt B):3-46).

The present invention also relates to methods and compositions for the treatment of cancer. Cancers, such as gastric cancer; breast cancer; pancreatic cancer; prostate cancer; uterine cancer; ovarian cancer; colon cancer; esophagus cancer; testicular cancer and lung cancer can be treated by inhibiting expression, biological activity or function of MH15. Reagents for inhibition of MH15 expression include, but are not limited to, anti-sense nucleic acid sequences that are complimentary to and will hybridize with MH15 mRNA in-vivo. Anti-sense nucleic acid sequences may be in the form of single stranded DNA or RNA molecules that hybridize to all or a part of the sequence of SEQ ID NO:1. Anti-sense oligonucleotides can also be used to inhibit expression of MH15 in target tissues. Anti-sense sequences can be administered directly to the tumour or can be transcribed from a vector that is transfected into the tumour cells. Transfection of tumour cells with suitable gene therapy vectors can be achieved using suitable liposomal delivery systems or viral vectors (Hughes R. M. J Surg Oncol. 2004 January; 85(1):28-35).

Inhibitors of MH15 biological activity and/or function can include antibodies, small molecules, polysaccharides and glycoproteins. Inhibitors of MH15 biological activity and/or function may act via a number of mechanisms such as by binding directly to the MH15 protein, or inhibiting a regulatory pathway that controls MH15 and thereby leads to suppression of MH15 function. Methods for screening candidate molecules for MH15 interactions are described in more detail below.

Particular small nucleic acid molecules that are of use in the invention are short stretches of double stranded RNA that are known as short interfering RNAs (siRNAs). These interfering RNA (RNAi) techniques allow for the selective inactivation of gene function in vivo. In the present invention, RNAi has been used to knock-down MH15 expression in the cancer cell line TOV112D and in doing so demonstrates dramatic effects on the malignancy of these cells. In this process, double stranded mRNAs are recognized and cleaved by the dicer RNase resulting in 21-23 nucleotide long stretches of RNAi. These RNAis are incorporated into and unwound by the RNA-inducing silencing complex (RISC). The single antisense strand then guides the RISC to mRNA containing the complementary sequence resulting in endonucleolytic cleavage of the mRNA, see Elbashir et al. (Nature 411; 494-498 (2001)). Hence, this technique provides a means for the targeting and degradation of MH15 mRNA in tumor cells in vivo.

Antibodies and fragments that specifically bind to MH15 polypeptides can be used to treat cancers. The invention includes the use of antibodies and antibody fragments that are fused to other moieties that can have a cytotoxic effect on cancer cells.

Pharmaceutical preparations of the invention are formulated to conform with regulatory standards and can be administered orally, intravenously, topically, or via other standard routes. The pharmaceutical preparations may be in the form of tablets, pills, lotions, gels, liquids, powders, suppositories, suspensions, liposomes, microparticles or other suitable formulations known in the art.

Vaccines that contain one or more of the MH15 polynucleotide, polypeptide, T-cell and/or antibody compositions described herein in combination with adjuvants, and that act for the purposes of prophylactic or therapeutic use, are also within the scope of the invention. The preparation of vaccines is generally described in, for example, M. F. Powell and M. J. Newman, eds., "Vaccine Design (the subunit and adjuvant approach)", Plenum Press (NY, 1995). MH15 polypeptide fragments or peptides may comprise an immunogenic epitope, which can be identified using standard methods (Geysen et al. Proc. Natl. Acad. Sci. USA 81: 3998 (1983)). Such epitope bearing peptides typically contain at least ten to fourteen amino acid residues of SEQ ID NO: 2, and can be produced by fragmenting the MH15 polypeptide.

The invention also provides methods of treatment (prophylactic and/or therapeutic) for cancers using a therapeutic agent comprising polynucleotide, polypeptide, T-cell and/or antibody described herein.

The MH15 polypeptides of the present invention can be produced in recombinant host cells according to conventional techniques (Sambrook J. et al, Molecular Cloning: a Laboratory Manual, Cold Spring Harbor Press, Cold Spring Harbor, N.Y.). Suitable host cells are those that can be grown in culture and are amenable to transformation with exogenous DNA, including bacteria, fungal cells and cells of higher eukaryotic origin, preferably mammalian cells.

MH15 polypeptides of the present invention can be used to identify other proteins and polypeptides that interact with MH15 in the cellular environment. Conventional techniques for determining protein-protein interactions, such as the yeast two-hybrid screen, can be used to identify potential agonists and antagonists of MH15 activity.

MH15 protein-protein interactions or protein-small molecule interactions can be investigated using technologies such as a BlAcore® which detects molecular interactions using surface plasmon resonance (BlAcore, Inc., Piscataway, N.J).

Screening of molecules and proteins for binding to MH15 protein can be performed via automated high-throughput screening procedures. Hence, the invention provides methods for identifying MH15 interacting molecules via detection of a positive binding interaction between MH15 and a target molecule. Further screening steps may be used to determine whether the identified positive binding interaction is of pharmacological importance—i.e. whether the target molecule is capable of moderating MH15 biological activity or function. If a molecule with a positive MH15 moderating effect is identified, the molecule is classified as a 'hit' and can then be assessed as a potential candidate drug. Additional factors may be taken into consideration at this time or before, such as the absorption, distribution, metabolism and excretion (ADME), bio-availability and toxicity profiles of the molecule, for example. If the potential drug molecule satisfies the pharmacological requirements it is deemed to be pharmaceutically compatible. Suitable compositions can be formulated for testing the activity in-vitro and in-vivo in accordance with standard procedures known in the art.

Accordingly, it is within the scope of the invention to further use a candidate drug identified above in an appropriate animal model, in order to further determine the efficacy, toxicity, or side effects of treatment with such agents. Also, the agent(s) identified above can be used in an animal model to determine the mechanism of action of such agents. The potentially valuable molecules or prodrugs for the prevention and/or treatment of cancers and/or other diseases or disorders can thus be screened in the platforms and assays as described above.

The invention is further illustrated by the following non-limiting examples.

EXAMPLES

Example 1

RT-PCR of MH15 in Peripheral Blood Mononuclear Cells from a Healthy Volunteer and Cancer Cell Lines I. Materials and Methods A. Blood Sample:

Fresh peripheral venous blood collected from a healthy volunteer was used as control, and peripheral blood mononuclear cells (PBMCs) were isolated there from using Ficoll-Paque plus (Amersham Biosciences).

B. Human Cell Lines:

Human cell lines such as a gastric cancer cell line (KATO III), breast cancer cell lines (MDA-MB-435S, MCF 7), hepatoma cell lines (Hep3B, HepG2), a prostate cancer cell line (DU 145), an esophageal cancer cell line (CE 146T/VGH), kidney cell lines (293, 293T) and a lung cancer cell line (NCI-H146) were purchased from BCRC, Taiwan. The cell lines, KATOIII and NCI-H146, were maintained in RPMI 1640 (Life Technologies, Inc.) supplemented with 10% fetal calf serum. The 293, 293T, DU 145, MDA-MB-435S and MCF 7 cell lines were maintained in DMEM (Life Technologies, Inc.) supplemented with 10% fetal calf serum. The Hep3B, HepG2 and CE 146T/VGH cell lines were maintained in DMEM with NEAA (Life Technologies, Inc.) supplemented with 10% fetal calf serum.

C. RNA Preparation:

The single step RNA isolation method was performed for RNA preparation by using TRIzol Reagent. In brief, PBMC cells or cell lines were homogenized in a TRIzol Reagent (Invitrogen, Life Technologies, Inc.) and put at room temperature (RT) for 5 min. 200µl chloroform was added and the mixture was vortexed for 15 sec. and put at room temperature (RT) for 3 min. After centrifugation, the RNA in the upper aqueous phase was precipitated with an equal volume of isopropanol and incubated for longer than 40 min, washed with 75% ethanol and dried under vacuum. The RNA pellet was then re-suspended in diethyl pyrocarbonate (DEPC)-treated water, and the final RNA concentration was determined spectrophotometrically by measuring the absorbance at 260 nm and 280 nm (GeneQuant pro RNA/DNA Calculator, Amersham Pharmacia Biotech, England).

D. Reverse Transcription-PCR Analysis:

Total RNA (5 µg) was reverse-transcribed using M-MLV Reverse Transcriptase (Invitrogen, Life Technologies, Inc.). Samples were amplified with PCR in a final reaction volume of 25 µl containing 2.5 µl of 10 times buffer (Amersham Pharmacia Biotech.), 0.1µl of 10 mM dNTPs, 10 pmoles of each primer and 0.5 units of Taq DNA Polymerase (Amersham Pharmacia Biotech.). To confirm the presence and integrity of the cDNA template, the housekeeping gene, GAPDH, was amplified for each sample using primers GAPDH-5 (5'-ACCACAGTCCATGCCATCAC-3'; SEQ ID NO: 3) and GAPDH-3 (5'-TCCACCACCCTGTTGCTGTA-3'; SEQ ID NO: 4). Conditions were as follows: an initial denaturation step for 5 minutes at 94° C., then 50 seconds at 94° C., 45 seconds at 55° C., and 1 min at 72° C. for 30 cycles, followed by an elongation step for 10 minutes at 72° C.

MH15 RT-PCR was performed using the following primers: primer F (5'-CCAACAGAAGAACCTCAGAAC-3'; SEQ ID NO: 5) and primer R (5'-CTCCTTGCAGCTTTAA-GATCC-3'; SEQ ID NO: 6). The parameters were as follows: The first denaturation step was at 94° C. for 4 minutes, followed by 35 cycles of denaturation at 94° C. for 50 seconds; Primer annealing occurred at 55° C. for 45 seconds, and elongation at 72° C. for 1 min. The final elongation step was conducted at 72° C. for 10 minutes.

II. Results

MH15 mRNA expression was first analyzed in PBMC cells from healthy individuals and cancer cell lines using RT-PCR technique. The amplified PCR products were analyzed by electrophoresis, and the result was shown in FIGS. 2A and 2B, which represents the mRNA expression of MH15 and GAPDH, respectively. 12.5 µl of every RT-PCR product was loaded in each lane. In FIGS. 2A and 2B, the mRNA used for RT-PCR is extracted from samples: PBMC from a healthy individual (lane 1), a gastric cancer cell line (KATOIII, lane 2), breast cancer cell lines (MDA-MB-435S, lane 3; MCF 7, lane 6), hepatoma cell lines (Hep3B, lane 4; HepG2, lane 10), a prostate cancer cell line (DU 145, lane 5), an esophagus cancer cell line (CE 146T/VGH, lane 7), kidney cell lines (293, lane 8; 293T, lane 9) and a lung cancer cell line (NCI-H146, lane 11), and M denotes the molecular size marker.

FIG. 2A shows the MH15 RT-PCR product with the expected molecular weight of 248 bp. It is noted that in FIG. 2A, the mRNA expression level of MH15 is elevated in cancer cell lines (lanes 2-11) when compared to that in the PBMC from a healthy individual (lane 1), while in contrast, FIG. 2B shows that mRNA expression level of GAPDH, a housekeeping gene, appears no significant difference in all tested samples.

Example 2

Northern Blot Analysis of MH15 in Peripheral Blood Mononuclear Cells and Cancer Cell Lines I. Materials and Methods A. Blood Sample:

PBMC from a healthy volunteer was prepared as previously described in example 1.

B. Cell Lines:

A gastric cancer cell line (KATO III), breast cancer cell lines (MDA-MB-435S, MCF 7), a hepatoma cell line (HepG2), a prostate cancer cell line (DU 145), an esophagus cancer cell line (CE 146T/VGH), a kidney cell line (293T), a lung cancer cell line (NCI-H23) and a lung cell line (MRC-5) were used. All cell lines were purchased from BCRC, Taiwan.

The cell lines, KATO III and NCI-H23, were maintained in RPMI 1640 (Life Technologies, Inc.) supplemented with 10% fetal calf serum. The cell lines, 293T, DU 145, MDA-MB-435S, MCF 7 and MRC-5, were maintained in DMEM (Life Technologies, Inc.) supplemented with 10% fetal calf serum. The cell lines, HepG2 and CE 146T/VGH, were maintained in DMEM with NEAA (Life Technologies, Inc.) and supplemented with 10% fetal calf serum.

C. Northern Blot Analysis:

Total RNA derived from different cancer lines and PBMC were isolated from different cell lines. The single step RNA isolation method was used for RNA preparation as previously described. 20 μg of total RNA from PBMC or cancer cell lines were separated by electrophoresis on 1% agarose gels containing formaldehyde and transferred to a nylon filter (Immobilon-NY+, Millipore corporation). Blots were prehybridized at 42° C. for 1 hour in an ExpressHyb™ Hybridization Solution (Clontech, Palo Alto, Calif.), and then hybridized at 60° C. for 24 hours with CCDNBP1 DNA probe, which were radiolabeled with [α-$^{32}$P]dCTP (3000 Ci/mL; New England Nuclear) with use of a random priming method (Rediprime random primer labelling kit, Amersham). Blots were washed and autoradiographed with x-ray film at −70° C.

II. Result

As shown in FIG. 3A, the expression of human MH15 in different cancer lines and PBMC are shown as follows: a Hep G2 cell line (lane 1), a KATO III cell line (lane 2), a MCF 7 cell line (lane 3), a MDA-MB-435S cell line (lane 4), a DU 145 cell line (lane 5), a CE 146T/VGH cell line (lane 6), a NCI-H23 cell line (lane 7), a MRC-5 cell line (lane 8) a 293T cell line (lane 9) and a PBMC sample from a healthy volunteer (lane 10). FIG. 3B shows the 18S and 28S RNA as a control. 10 μg of the product from Northern blot was loaded in each lane. The size of the MH15 cDNA was estimated to be approximately 3.5 AND 4 kb. MH15 is differentially expressed in various kinds of cancer cell lines, whereas is barely detectable in PBMCs of healthy volunteers.

Example 3

Detection of MH15 in Peripheral Blood Mononuclear Cells from Gastric Cancer Patients Gastric cancer has a high mortality rate in many countries, particularly Taiwan, America, Japan and China. In order to determine whether MH15 is a potential biomarker for gastric cancer, the expression of MH15 mRNA in peripheral blood mononuclear cells (PBMC) from both gastric cancer patients and healthy individuals was examined with RT-PCR and real time PCR techniques.

I. Materials and Methods

A. Blood Sample:

Peripheral venous blood samples were collected from 10 patients with gastric cancer. Also, peripheral venous blood samples from 10 healthy volunteers were obtained as controls. Patient samples were collected at National Taiwan University Hospital, Taiwan. Peripheral blood mononuclear cells (PBMC) were isolated from freshly collected citrated venous blood using Ficoll-Paque (Amersham Biosciences).

B. Reverse Transcription-PCR Analysis:

The single step RNA isolation method was used for RNA preparation as previously described, and RT-PCR analysis was performed as previously described in example 1.

C. Real Time PCR Analysis:

The single step RNA isolation method was used for RNA preparation as previously described, and Real Time-PCR analysis was performed as ABI protocols. Total RNA (2 μg) was reverse-transcribed using M-MLV Reverse Transcriptase (Invitrogen, Life Technologies, Inc.). 5 μl of cDNA were amplified with Applied Biosystems 7500 Real-Time PCR System in a final reaction volume of 25 μl containing 12.5 μl of 2 times Taq master mix buffer (Applied Biosystems), 1.25μl of 20 times TaqMan Gene Expression Assay (Applied Biosystems, Hs00298954_ml), and 1.25 μl of water. To confirm the presence and integrity of the cDNA template, the housekeeping gene, GAPDH, was amplified for each sample using Hs99999905_ml (Applied Biosystems). Conditions were as follows: an initial step for 2 minutes at 50° C., 10 minutes at 95° C., then 15 seconds at 95° C. and 1 minute at 600C for 40 cycles.

II. Results

Table I show the gene expression of MH15 and GAPDH, respectively. The mRNA samples were isolated from PBMC cells from healthy individuals (sample 1-6) and gastric cancer patients (sample 7-11), and the expression level of mRNA was analyzed by the RT-PCR technique. 12.5 μl of every RT-PCR product was loaded in each lane. The mRNA expression level of MH15 significantly increased in PBMC cells of gastric cancer patients (sample 7, 9, 10 and 11) when compared to that of healthy individuals (sample 1-6), while in contrast, there appears no distinguishable difference in any of the tested samples in the mRNA expression level of GAPDH.

Table II shows the gene expression of MH15 and GAPDH by real time PCR, respectively. The mRNA samples were isolated from PBMC cells from healthy individuals (sample 1-4) and gastric cancer patients (sample 5-9), and the expression level of mRNA was analyzed by real time PCR. The mRNA expression level of MH15 significantly increased in PBMC cells of gastric cancer patients (sample 5, 6, 8 and 9) when compared to that of healthy individuals (sample 1-4).

Example 4

In Vitro Transforming and In Vivo Tumorigenic Activities of MH15

In order to determine whether MH15 is a potential oncogene, MH15 was transfected into NIH 3T3 cells and the change in the growth properties induced by MH15 overexpression were assayed by a series of experiments.

I. Material and Methods

A. Stable Transfection of MH15

NIH-3T3 cells were cultured in DMEM with 10% FBS at 37° C. The human MH15 coding sequence was cloned from KATO III cellular RNA with oligonucleotide primers (F-primer: 5'-ATGTTCCAGGTCCCGGATAG-3' SEQ ID NO: 7 and R-primer: 5'-TTAGTAGAAGGAGATGCTGG-3' SEQ ID NO: 8) to amplify this gene. cDNA was synthesized by reverse transcriptase (Invitrogen) with Oligo dT primer and PCR amplified by Taq polymerase (Amersham Biosciences). The PCR product was then cloned into pGEM-T-Easy Vector (Promega). For transfection, MH15 was subcloned into pcDNA 3.1. This vector was introduced into NIH-3T3 cells by lipofectamine 2000 (Invitrogen, California, U.S.A.). The transfected cells were then cultured in complete medium containing 600 μg/mL geneticin (G418) for selecting of recombinant clones expressing G418 resistance. After 4 weeks, individual surviving clones in the presence of G418 were further expanded into a mass culture and the gene expression was examined by RT-PCR. The high expression clones were selected and subjected to transforming activity assays such as growth rate, focus formation, and anchorage independent growth in soft agar.

B. Cell Cycle Analysis

For cell cycle analysis, exponential growing cells ($1\times10^6$) were first trypsinized and fixed in 70% ethanol at −20° C. for 2 h, followed by treating with 10 μg/mL RNase A at 37° C. for 1 h and then stained with 50 μg/mL propidium iodide at room temperature in our dark room for 30 min. The stained cells were analyzed by flow-cytometer (PAS-II; Partec AG, Munster, Germany). Single-channel data were obtained and subsequently analyzed with a computer program (Phoenix Flow Systems, San Diego, Calif.) that is able to generate a plot of the number of cells versus DNA contents and the percentage of cells in cell cycle phases.

C. Anchorage Independent Growth in Soft Agar

For anchorage independent growth in soft agar, NIH-3T3 cells and MH15 transfectants were first suspended in a 2 ml 0.3% agar containing a complete medium and 20% FBS, and then were layered on a 1.5 ml solidified 0.6% agar in a complete medium and 20% FBS. Surviving colonies were developed with 2 mg/ml MTT solution at 37° C. for 12 h.

D. Tumorigenesis and Metastasis

Six to eight-week-old athymic nu/nu BALB/c mice obtained from the National Laboratory Animal Center, Taiwan, were used in tumorigenic experiments. Animal care was provided in accordance with the procedures outlined in the *Guide for the Care and Use of Laboratory Animals* (NIH Publication No. 86-23, 1985). To assess tumorigenesis, parental and transfectant cells ($2\times10^6$) were suspended in 100 μl PBS and injected subcutaneously into posterior lateral aspect of the mice. Large (D) and small (d) diameters of growing tumors were measured twice a week, and the corresponding volumes (V) were estimated using the equation: $V=width^2\times length\times 0.5$. For the analysis of metastasis, $5\times10^6$ cells in 100 μl were injected intravascularly into the tail vein of nude mice. Mice survival was followed and recorded. Surviving mice were killed after 5 weeks to examine metastatic nodules.

II. Results

A. In Vitro Transforming Activity

Figure 4A:
FIG. 4A shows the RT-PCR result of MH15 expression level in MH15-transfected NIH 3T3 cells.
Figure 4B:
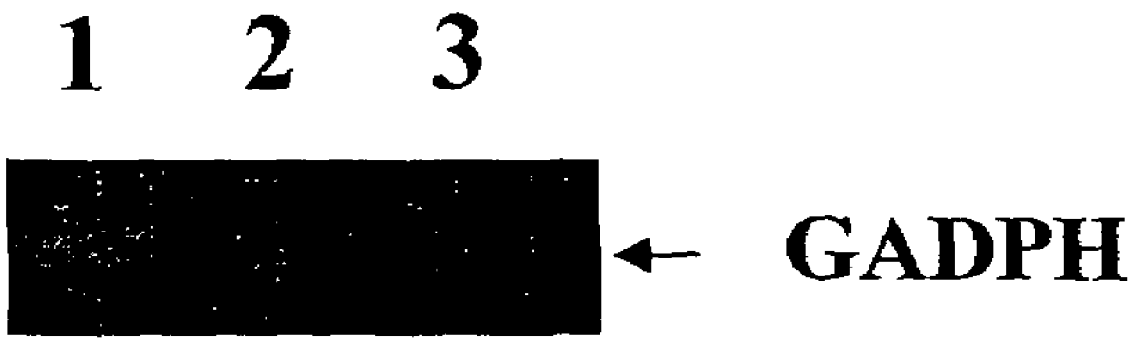
FIG. 4B shows the RT-PCR result of GAPDH expression level in MH15-transfected NIH 3T3 cells.

To assess the transforming potential of MH15, the expression vectors containing MH15 coding sequence was transfected into NIH-3T3 cells. MH15 transfectants were obtained by G418 selection, and the expression level of MH15 in parental and transfected cells was confirmed by RT-PCR analysis as shown in FIG. 4 (lane 1: NIH3T3; lane 2: MH15-4; lane 3: MH15-11). Three independent transfectants, parental NIH-3T3(lane 1), MH15-4(lane 2) and MH15-11(lane 3).

Three independent transfectants were selected for transforming activity assays, including growth rate determination, morphology inspection, cell cycle progression examination, and anchorage independent growth in soft agar. As shown in FIG. 5, the transfectants exhibited morphologically transformed cell foci comprised of individual spindle-shaped cells characterized by a dense, disorganized pattern of growth, and increased refractivity (FIGS. 5C and 5D), while cells transfected with control vector retained a normal cell morphology (FIG. 5B). The tumorigenecity of MG-20 transfectants in vitro was also evaluated with clonogenic growth in soft agar before in vivo tests. This in vitro assay is known to be most closely related to in vivo tumorigenesis. MH15 transfected cells were able to form survival colonies in semisolid medium after MTT staining. TAB. III displays the proliferative properties of the transfected cell lines. A shorter doubling time and cell cycle progression from G1 to S phase were found in MH15 transfectants, but not in parental and vector control cells. The results in combination strongly suggest that MH15 is an oncogene that can transform NIH-3T3 cells.

B. In Vivo Tumorigenic and Metastatic Activity

Figure 6:
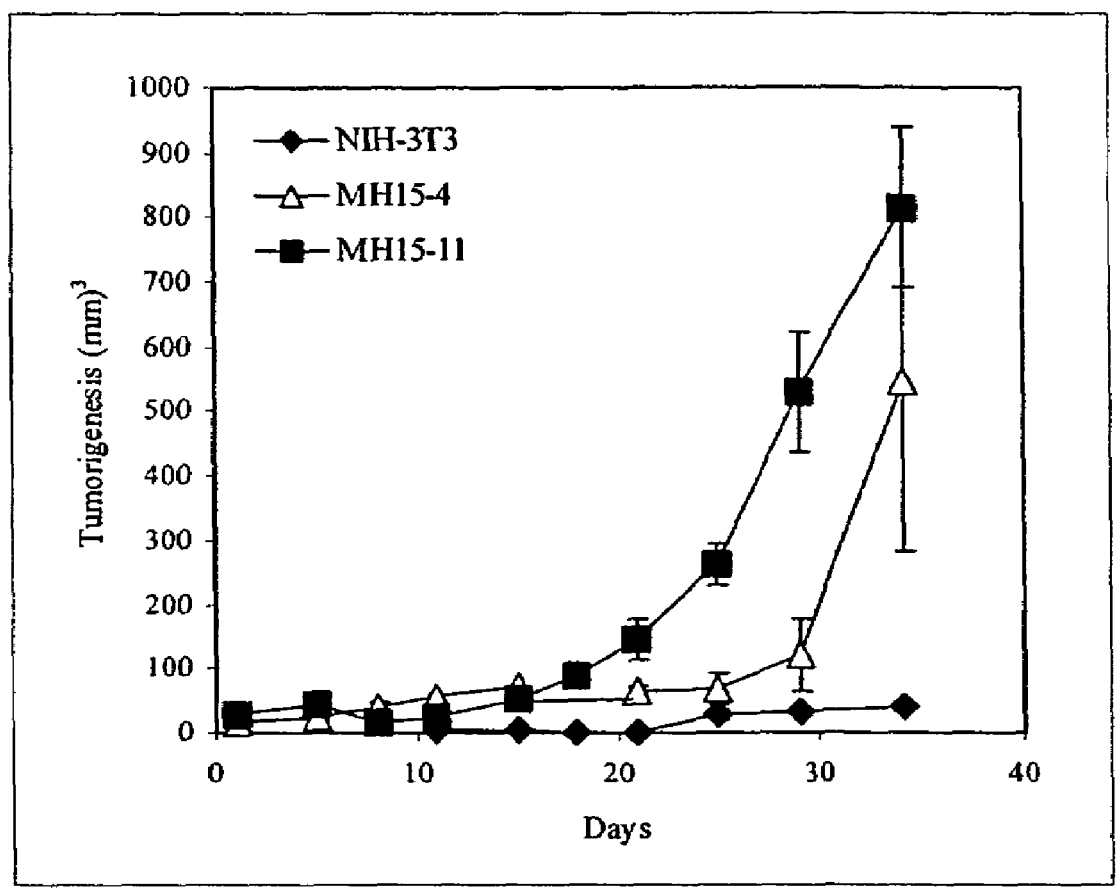
FIG. 6 shows the tumor development induced by MH15 over-expression in NIH 3T3 cells.

To assess the ability of MH15 to induce tumor formation in vivo, MH15-4 and MH15-11 and parental NIH-3T3 cells were injected s.c. into nude mice. The animals injected with MH15-11 and MH15-4 cells possessed rapidly growing tumors by 15 days and 21 days, respectively, whereas none of the animals injected with parental cells had tumors (FIG. 6). After 33 days, the tumorigenicity of MH15-11 was evident with a mean tumor size approaching 1000 mm$^3$. All of the data clearly demonstrate that MH15 has potent growth-stimulating potential in vitro and oncogenic potential in vivo.

The metastatic potential of the MH15 transfectants are displayed in FIG. 7. Metastatic nodules, mostly in the intestinal and gastric walls, were found in the mice with MH15-tranfected cells, whereas no tumor was formed in the mice with parental cells or vector control cells even after 55 days. Mice did not die with parental cells and vector control cells (FIG. 7).

Example 5

Clinical Relevance of MH15 Expression Level with Cancer

In order to determine the clinical relevance with cancer development, MH15 mRNA levels are measured in various kinds of cancer patients using RNA profiling assay.

I. Material and Methods

The cancer profiling array II which has been spotted with a variety of cancer tissue RNAs on a nylon membrane was purchased from Clontech, Palo Alto, Calif. The membrane contains a parallel array of normal (N) and malignant (T) RNAs of 19 different tissues including breast, ovarian, colon, stomach, lung, kidney, bladder, vulva, prostate, trachea, liver, uterus, cervix, rectum, thyroid gland, testis, skin, small intestine and pancreas. The RNAs of normal (N) or malignant tissues (T) were arranged in pairs, with each pair representing a particular type of normal and cancerous tissue from a single patient. For a single type of cancer, each line contains tissues from 3-10 patients. For the purpose of comparison, an additional 9 cell lines, including HeLa, Daudi, K562, HL60, G361, A549, MOLT4, SW480 and Raji were also spotted on the membrane. Profiling array was prehybridized at 68° C. for at least 30 mins in an ExpressHyb™ Hybridization Solution (Clontech, Palo Alto, Calif.), and then was further hybridized at 68° C. for 24 hours with MH15 DNA probes, which were radiolabeled with [α-$^{32}$P]dCTP 3000 Ci/mL (New England Nuclear) using of a random priming method (Rediprime random primer labelling kit, Amersham). Blots were washed and then autoradiographed with x-ray film at −70° C.

II. Results

Figure 8A:
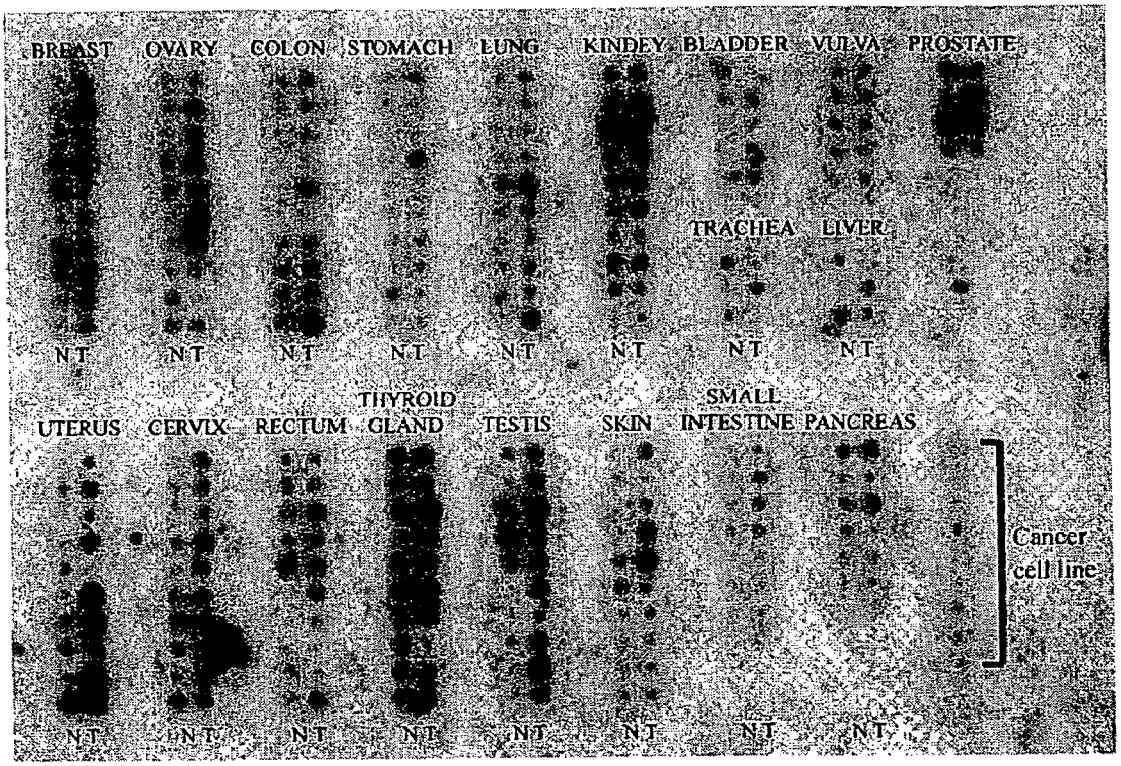
FIG. 8A shows the result of RNA profiling assay for MH15 expression in cancer and adjacent normal tissues.
Figure 8B:
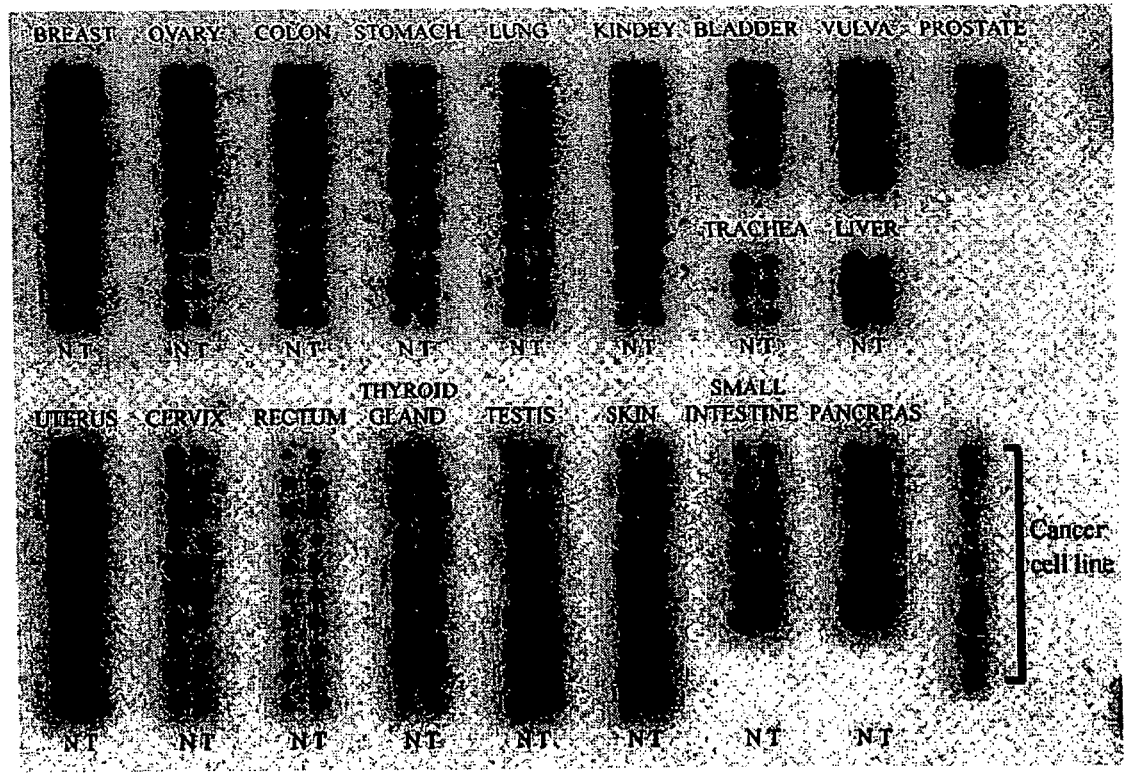
FIG. 8B shows the result of RNA profiling assay for ubiquitin.

FIG. 8A shows the result of RNA profiling assay for MH15 expression in cancer and adjacent normal tissue. Significantly higher expression of MH15 was especially found in the cancer of gastric cancer, breast cancer, pancreatic cancer, prostate cancer, uterine cancer, ovarian cancer, colon cancer, esophagus cancer, testicular cancer and lung cancer, which, in turn, suggests that MH15 plays an important role in these cancers.

Example 6

Knockdown of MH15 Expression Reduces Cell Malignancy

I. Materials and Methods

A. Antibody Production

For producing the antibody, GST fusion protein of MH15 was overexpressed as an antigen in *E. coli* system and electrophoresed by SDS-PAGE. The purified GST-MH15 was contracted out to Cho Shui Shi Corp., Taiwan for antibody induction. Twenty mg of target protein and 2 ml of Freund's adjuvant was injected subcutaneously to a New Zealand white rabbit monthly. Blood samples were collected on a monthly basis after the second injection, and then the titer was analyzed. When the titer was acceptable, blood was sampled for serum collection. The contamination of antibody recognizing GST only was screened out using the GST column and then the MH15 antibody was purified through the MH15 affinity column.

B. RNAi

RNAi-mediated reduction in gene expression is performed by transfecting synthetic 19-21 nt double-stranded RNA. RNAi technology was used to explore the anti-tumor activity of these RNAis for MH15 through reducing the expression level of MH15. To obtain the best knock-down or silencing effect, the RNAi construct was cloned by using oligonucleotide primers (5'-GATCCCCGGAGGAGAATCGAG-CAATCTTTTCAAGAGAAAGATTGCTC-GATTCTCCTCCTTTTA-3' SEQ ID NO: 9 and 5'-AGCTTAAAAAGGAGGAGAATCGAG-CAATCTTTCTCTTGAAAAGATTGCTC-GATTCTCCTCCGGG-3' SEQ ID NO: 10). The MH15-ShRNA fragments were amplified by PCR reaction with Taq polymerase (Amersham Biosciences). The PCR product was cloned into pSUPER.retro.neo vector□OligoEngine□

C. Transfection of MH15-shRNA

TOV112D cells were cultured in MCDB 105 with 15% FBS at 37° C. The MH15-shRNA and pSUPER.retro.neo vector with irrelevant sequences were introduced into TOV112D cells by lipofectamine 2000 (Invitrogen, California, U.S.A.). The transfected cells were then cultured in complete medium containing 600 µg/mL G418 for selecting of recombinant clones expressing puromycin resistance. After 5 days, all the transfectant cells were photographed and the gene expression was examined by RT-PCR and western blotting.

D. Tumorigenesis

Six to eight-week-old athymic nu/nu BALB/c mice obtained from the National Laboratory Animal Center, Taiwan, were used in tumorigenic experiments. Animal care was provided in accordance with the procedures outlined in the *Guide for the Care and Use of Laboratory Animals* (NIH Publication No. 86-23, 1985). To assess tumorigenesis, parental and transfectant cells ($2 \times 10^6$) were suspended in 100 µl PBS and injected subcutaneously into the posterior lateral aspect of the mice. Large (D) and small (d) diameters of growing tumors were measured twice a week, and the corresponding volumes (V) were estimated using the equation: $V = width^2 \times length \times 0.5$. For the analysis of metastasis, $5 \times 10^6$ cells in 100 µl were injected intravascularly into the tail vein of nude mice. Mice survival was followed and recorded. Surviving mice were killed after 5 weeks to examine metastatic nodules.

II. Results

Interference of gene expression by small interfering RNA (RNAi) is now recognized as a natural biological strategy for silencing gene expression. RNAi technology allows for gene-specific knock-down without induction of the non-specific interferon response in mammalian cells. We use RNAi targeting MH15 as an agent to reduce the expression level of MH15 and study the anti-malignancy effect of such agents.

A. RNAi Reduces Endogenous MH15 Expression Levels in Cancer Cells.

FIG. 9A shows the reduction of MH15 levels in MH15-shRNA transfectants. Using the amount of GAPDH as an internal control, it is obvious that the MH15 levels in shRNA containing cells is significantly lower than in cells without shRNA. Compared to the parental TOV112D cells, the relative amount of MH15 RNA expression was 36% lower in TOV112D cells with MH15-shRNA constructs (TAB. IV). At the protein level, the relative amount of MH15 protein expression was 50% lower in TOV112D cells with MH15-shRNA constructs (FIG. 9B, TAB. IV).

B. Cancer Cells with Reduced MH15 Level Exhibit Less Malignant Characteristics.

Figure 10:
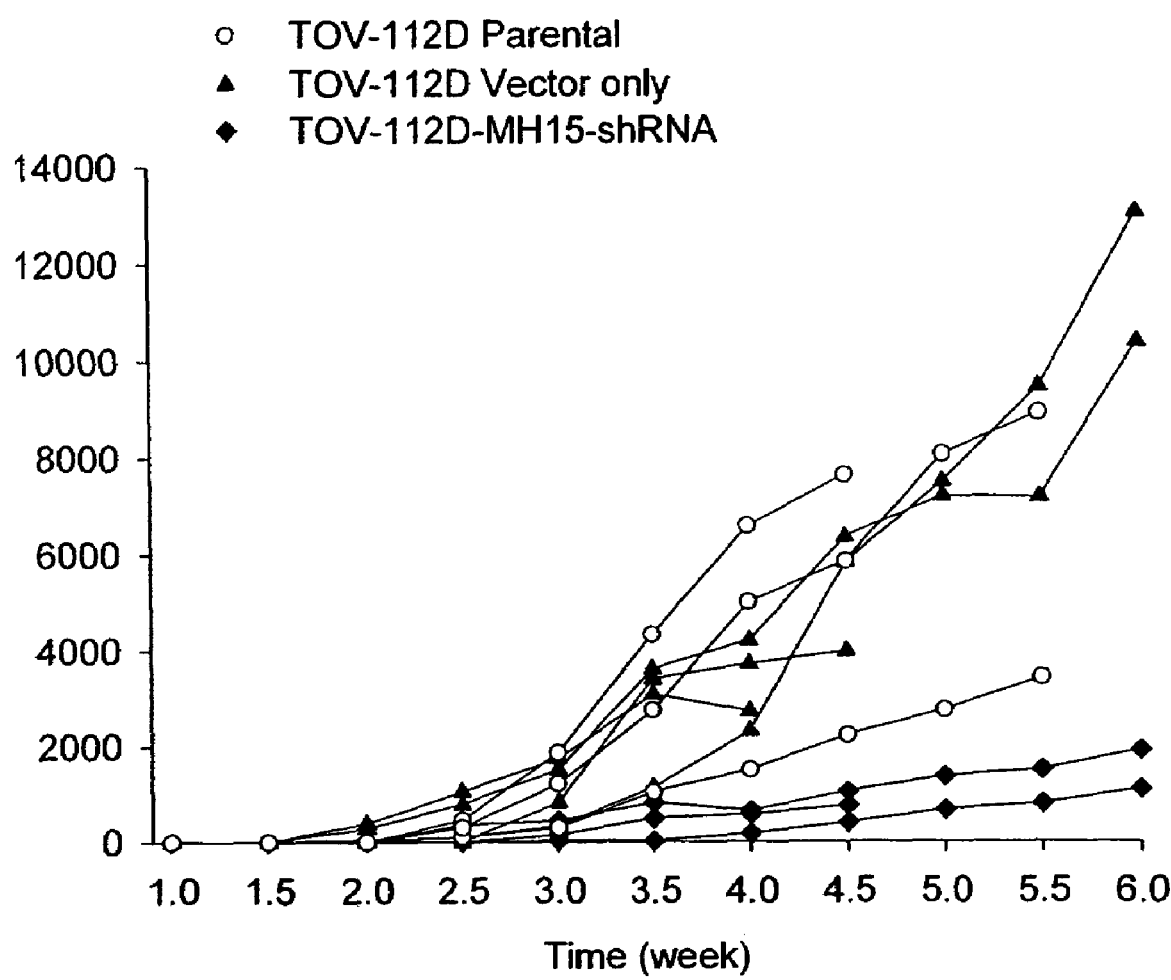
FIG. 10 shows the tumor development reduced by MH15 targeting shRNA in TOV112D cells.

To assess the ability of MH15-shRNA to reduce tumor formation in vivo, TOV112D transfected with vector only, MH15-ShRNA and parental TOV112D cells were injected s.c. into nude mice. The animals injected with parental cells and transfectant with vector only possessed rapidly growing tumors by 15 days and 21 days, respectively, whereas lower volume tumors appeared in the animals injected with MH15-ShRNA transfectants (FIG. 10). After 42 days, the tumorigenicity of parental cells and transfectants with vector only was evident with a mean tumor size approaching 12000 mm³, while the tumor growth was less than 2000 mm³ in MH15-ShRNA transfectants. All the data clearly demonstrates that MH15-ShRNA has potent growth-inhibiting potential in vitro and tumor suppressor potential in vivo. This result demonstrates the feasibility of using inhibitors of MH15 expression or function in treating malignancy in tumor cells.

TABLE I

Quantification of RT-PCR in 6 healthy volunteers and 5 gastric cancer patients' PBMC. Statistically significant difference is evaluated using a one-tailed Student's t-test.

| sample | MH15 Q# | sample type | sample number | GAPDH Q# | MH15 Q#/ GAPDH Q# | Normal average = 0.2495 (MH15 Q#/GAPDHQ#)/ Normal average |
|---|---|---|---|---|---|---|
| 1 | 8449 | Normal | healthy volunteer 13 blood | 37430 | 0.2257 | 0.905 |
| 2 | 9377 | Normal | healthy volunteer 14 blood | 37018 | 0.2533 | 1.015 |
| 3 | 8245 | Normal | healthy volunteer 15 blood | 38645 | 0.2134 | 0.855 |
| 4 | 9595 | Normal | healthy volunteer 17 blood | 35297 | 0.2718 | 1.089 |
| 5 | 10631 | Normal | healthy volunteer 18 blood | 39832 | 0.2669 | 1.070 |
| 6 | 9299 | Normal | healthy volunteer 19 blood | 34963 | 0.2660 | 1.066 |
| 7 | 11020 | Gastric Cancer | Patient G211 blood | 33304 | 0.3309 | 1.326 |
| 8 | 9316 | Gastric Cancer | Patient G212 blood | 33968 | 0.2743 | 1.099 |
| 9 | 13770 | Gastric Cancer | Patient G213 blood | 34011 | 0.4049 | 1.623 |
| 10 | 14998 | Gastric Cancer | Patient G214 blood | 34406 | 0.4359 | 1.747 |
| 11 | 14719 | Gastric Cancer | Patient G215 blood | 34151 | 0.4310 | 1.727 | p value <0.05

TABLE II

Real Time-PCR in 4 healthy volunteers and 5 gastric cancer patients' PBMC.

| | sample type | sample number | Avg. GAPDH Ct | Avg. H15 Ct | Avg. dCt | $2^{-dCt}$ | Normal average = 0.0020 $2^{-dCt}$/Normal average |
|---|---|---|---|---|---|---|---|
| 1 | Normal | healthy volunteer 211 blood | 20.947i ±.048 | 29.898i ±.102 | 8.951i ±.113 | 0.00202 | 1.0210 |
| 2 | Normal | healthy volunteer 22 blood | 19.906i ±.094 | 29.474i ±.050 | 9.568i ±.106 | 0.00132 | 0.6657 |
| 3 | Normal | healthy volunteer 23 blood | 20.916i ±.041 | 29.740i ±.002 | 8.823i ±.041 | 0.00221 | 1.1158 |
| 4 | Normal | healthy volunteer 24 blood | 20.955i ±.013 | 29.677i ±.006 | 8.721i ±.015 | 0.00237 | 1.1975 |
| 5 | Gastric Cancer | Patient G222 blood | 21.065i ±.059 | 28.889i ±.308 | 7.823i ±.314 | 0.00442 | 2.2315 |
| 6 | Gastric Cancer | Patient G225 blood | 21.580i ±.047 | 29.984i ±.003 | 8.404i ±.047 | 0.00295 | 1.4918 |
| 7 | Gastric Cancer | Patient G226 blood | 22.430i ±.073 | 32.094i ±.181 | 9.663i ±.195 | 0.00123 | 0.6233 |
| 8 | Gastric Cancer | Patient G227 blood | 22.641i ±.075 | 30.056i ±.024 | 7.415i ±.079 | 0.00586 | 2.9609 |
| 9 | Gastric Cancer | Patient G228 blood | 21.858i ±.020 | 30.203i ±.085 | 8.345i ±.087 | 0.00308 | 1.5540 |

TABLE III

Transforming properties of MH15 over-expressed NIH-3T3 cells.

| Cells[a] | Doubling time[b] | Focus formation[c] | Anchorage independent growth[d] |
|---|---|---|---|
| NIH-3T3 | 25.2 i ±0.4 | 0 | 6.0 i ±1.1 |
| Vector | 26.0 i ±6.7 | 0 | 3.0 i ±0 |
| MH15-4 | 19.7 i ±1.2 | 12.7 12.7 i ±2.2 | 17.7 i ±0.7 |
| MH15-11 | 18.6 i ±1.2 | 15.0 i ±1.2 | 56.1 i ±1.3 |

[a]MH15-4/MH15-11, two clones of the MH15 over-expressed NIH-3T3 cells.
[b]calculated during the exponential growth phase.
[c]$1 \times 10^5$ cells plated in 100 mm dish and changed medium every 3 days. 2 weeks later, the colonies formed the on dish was scored.
[d]Cells (500/dish) were plated in 0.3% soft agar and 20% serum. 20 days later, the colonies containing more than 100 mm were scored.

TABLE IV

Quantification of the gel shown in FIG. 9 of a RT-PCR assay for MH15 and GAPDH gene transcripts and a western blotting assay for MH15 and Actin gene translations in TOV112D or MH15-ShRNA stable cell clones.

| | Parental | Vector only | MH15-shRNA |
|---|---|---|---|
| | RNA Expression of MH15 | | |
| MH15 | 34288 | 30395 | 20394 |
| GAPDH | 84723 | 78718 | 82645 |
| MH15/GAPDH | 0.4047 | 03861 | 0.2468 |
| MH15 expression in MH15-shRNA Vector only | | | 63.9% |
| MH15 expression reducing in MH15-shRNA | | | 36.1% |
| Protein Expression of MH15 | | | |
| MH15 | 252526 | 342789 | 156982 |
| Actin | 118415 | 100564 | 92579 |
| MH15/Actin | 2.1326 | 3.4087 | 1.6957 |
| MH15 expression in MH15-shRNA Vector only | | | 49.7% |
| MH15 expression reducing in MH15-shRNA | | | 50.3% |

Although particular embodiments of the invention have been disclosed herein in detail, this has been done by way of example and for the purposes of illustration only. The aforementioned embodiments are not intended to be limiting with respect to the scope of the appended claims, which follow. The choice of nucleic acid starting material, the clone of interest, or type of library used is believed to be a routine matter for the person of skill in the art with knowledge of the presently described embodiments. It is proposed by the inventors that various substitutions, alterations, and modifications may be made to the invention without departing from the spirit and scope of the invention as defined by the claims.

What is claimed is:

1. A method of detecting and diagnosing gastric cancer in a patient in need thereof, comprising the steps of:
   obtaining a biological sample comprising whole blood from said patient;
   analysing said biological sample for the expression of MH15 (also known as Hn1L), said analysing step comprising detecting mRNA encoded by the polynucleotide sequence set forth in SEQ ID NO: 1 in peripheral blood mononuclear cells (PBMCs) from the biological sample; and
   wherein expression of said mRNA in said PBMCs at levels in excess of the level of mRNA encoded by the polynucleotide sequence set forth in SEQ ID NO: 1 in PBMCs from a normal, healthy subject indicates that said patient has gastric cancer.

2. A method of detecting and diagnosing gastric cancer in a patient in need thereof, comprising the steps of:
   (a) providing a biological sample comprising whole blood from said patient;
   (b) detecting the level of MH15 (also known as Hn1L) mRNA encoded by the polynucleotide sequence set forth in SEQ ID NO: 1 in peripheral blood mononuclear cells (PBMCs) from the biological sample; and
   (c) comparing the level of MH15 mRNA in the biological sample with the level of MH15 mRNA encoded by the polynucleotide sequence set forth in SEQ ID NO: 1 in a control sample of PBMCs from from a normal, healthy subject;
   wherein an increased level of said MH15 mRNA in the biological sample compared to said MH15 mRNA in the control sample indicates the presence of gastric cancer in said patient.

3. The method according to claim 2, wherein said level of MH15 in said biological sample is detected by determining the mRNA level in said PBMCs with the use of a probe or primer selected from the group consisting of SEQ ID NO: 5; SEQ ID NO: 6; SEQ ID NO: 7 and SEQ ID NO: 8 that can hybridize with said MH15 mRNA or fragment thereof.

4. The method according to claim 1, wherein the mRNA level of MH15 is detected by a technique selected from the group consisting of: Northern blot; in situ hybridization; RNase protection; RT-PCR based techniques; RACE; branched DNA technology; nucleic acid hybridization-based techniques, and combinations thereof.

5. An in vitro method for monitoring the recurrence of gastric cancer in a patient who has been treated for cancer, comprising the steps of:
   (a) interacting a biological sample comprising whole blood from the patient with a substance selected from polynucleotides, probes or primers that interact with MH 15 (also known as Hn1L) mRNA encoded by the polynucleotide sequence set forth in SEQ ID NO: 1;
   (b) detecting the level of MH15 mRNA of SEQ ID NO: 1 that interacts with the substance in peripheral blood mononuclear cells (PBMCs) from the biological sample;
   (c) repeating steps (a) and (b) using a biological sample comprising whole blood from said patient at a subsequent point of time; and
   (d) comparing the level of said MH15 mRNA detected in step (c) with the level of MH15 mRNA encoded by the polynucleotide sequence set forth in SEQ ID NO: 1 detected in a control sample of PBMCs from a normal, healthy subject and therefrom determining the recurrence of gastric cancer in said patient,
   wherein a level of said mRNA detected in said biological sample in step (c) in excess of the level of said MH15 mRNA detected in the control sample is indicative of a recurrence of the gastric cancer in the patient.

* * * * *

SEQUENCE LISTING

```
<160> NUMBER OF SEQ ID NOS: 10

<210> SEQ ID NO 1
<211> LENGTH: 3040
<212> TYPE: DNA
<213> ORGANISM: Homo sapiens
<220> FEATURE:
<221> NAME/KEY: CDS
<222> LOCATION: (35)..(607)

<400> SEQUENCE: 1
ggcgcgcggc gagctgaggg tggcggcggt cgac atg ttc cag gtc ccg gat agc    55
```

```
                        Met Phe Gln Val Pro Asp Ser
                         1               5 gag ggc ggc cgc gcc ggc tcc agg gcc atg aag ccc cca gga gga gaa     103
Glu Gly Gly Arg Ala Gly Ser Arg Ala Met Lys Pro Pro Gly Gly Glu
         10              15              20 tcg agc aat ctt ttt gga agt cca gaa gaa gcc act cct tcc agc agg     151
Ser Ser Asn Leu Phe Gly Ser Pro Glu Glu Ala Thr Pro Ser Ser Arg
     25              30              35 cct aat agg atg gca tct aat att ttt gga cca aca gaa gaa cct cag     199
Pro Asn Arg Met Ala Ser Asn Ile Phe Gly Pro Thr Glu Glu Pro Gln
 40              45              50              55 aac ata ccc aag agg aca aat ccc cca ggg ggt aaa gga agt ggt atc     247
Asn Ile Pro Lys Arg Thr Asn Pro Pro Gly Gly Lys Gly Ser Gly Ile
             60              65              70 ttt gac gaa tca acc ccc gtg cag act cga cag cac ctg aac cca cct     295
Phe Asp Glu Ser Thr Pro Val Gln Thr Arg Gln His Leu Asn Pro Pro
         75              80              85 gga ggg aag acc agc gac att ttt ggg tct ccg gtc act gcc act tca     343
Gly Gly Lys Thr Ser Asp Ile Phe Gly Ser Pro Val Thr Ala Thr Ser
     90              95             100 cgc ttg gca cac cca aac aaa ccc aag gat cat gtt ttc tta tgt gaa     391
Arg Leu Ala His Pro Asn Lys Pro Lys Asp His Val Phe Leu Cys Glu
105             110             115 gga gaa gaa cca aaa tcg gat ctt aaa gct gca agg agc atc ccg gct     439
Gly Glu Glu Pro Lys Ser Asp Leu Lys Ala Ala Arg Ser Ile Pro Ala
120             125             130             135 gga gca gag cca ggt gag aaa ggc agc gcc aga aaa gca ggc ccc gcc     487
Gly Ala Glu Pro Gly Glu Lys Gly Ser Ala Arg Lys Ala Gly Pro Ala
             140             145             150 aag gag cag gag ccc atg ccc aca gtc gac agc cat gag ccc cgg ctg     535
Lys Glu Gln Glu Pro Met Pro Thr Val Asp Ser His Glu Pro Arg Leu
         155             160             165 ggg ccg cgg cct cgc tct cac aac aag gtc ctg aac cca ccg gga ggc     583
Gly Pro Arg Pro Arg Ser His Asn Lys Val Leu Asn Pro Pro Gly Gly
     170             175             180 aaa tcc agc atc tcc ttc tac taa gagaagccac tgctccaccc ggagccagac    637
Lys Ser Ser Ile Ser Phe Tyr
        185             190 cagaaactca agagataggg tagccatgtt ttcatttcct tttgcccaaa tgagcggggt    697
gggaagaggg ttagtcttat gtgagcctgg ctgctcagcg tctcctggcc gtcatgacag    757
ctgcttggag acccgtgcct tccagatggc tgggagatgc ctctgtgggg atgaaatggg    817
gcacccctgg ccatcactca tgtgtagtcc aggtttgaga ggaactggaa gggggtgag     877 ggtggggagg tggggcaggg catggtcctt ggatcaacag cccgccagct gattggatgt    937
ctaggaatga ctgaaagaaa ccaaaacagc ctgtccactg ctgctgtggg atggaggagg    997
cgtaagcaga aacactaaca gtatattgac ctcttagcag aaccgcttcc attctggaga   1057
tcacggctgc taaatccagc atccccactt cattttaccc ccagcatatt gttctgtagt   1117
cttttcttga aacatcttga ttgctttttc tcggcagctt tcaaaaaacc aaataataat   1177
agttatccgt cttctacttc atggaagatt gttttggtgc cctgaccctc tgaagtgccc   1237
agttcctgcc atctgaaacc tcggcctgat ctgatctcat gttggaatct gcctgtcttt   1297
cacacagggc tggtcttggt cctttacatg ccagttttgc ttgtgaattc ttgctttttt   1357
cctctcatca gccttaagtt taggcgtttg ttgttctcca gtgatgtaga cagttccctt   1417
cacaagtcac agttcttccc ataaatgagg cccgctgacc tctgcgggac tttaaaaatc   1477
```

-continued

```
tattcagata tttccgagta agtggcttgt ttaaattctt cctgtgtctt tctttattcc    1537
ttaattggtt ggtggaaaga agagatgctt gggaaccttg ggttcttagg tttggattct    1597
ttaataatat ctaaaaagct aaatttaaa taccagcttt acataaatga ttgttgactc     1657
tggtctgttt ctgacacctt tccagaaaaa agtcaattgt tcaggtacac caaagaggaa    1717
gaagagctgt ggaggccacc ctctacaaag ctttatagaa cttctggatc taactcacaa    1777
acaagcttcc agaagagact agagacctta ggccaggaga tgaaggagtt cagtagcaaa    1837
gtcacacctg tccaattccc tgagctttgc tcactcagct aatgggatgg caaaggtggt    1897
ggtgctttca tcttcaggca gaagcctctg cccatccccc tcaagggctg caggcccagt    1957
tctcatgctg cccttgggtg ggcatctgtt aacagaggag aacgtctggg tggcggcagc    2017
agctttgctc tgagtgccta caaagctaat gcttggtgct agaaacatca tcattattaa    2077
acttcagaaa agcagcagcc atgttcagtc aggctcatgc tgcctcactg cttaagtgcc    2137
tgcaggagcc gcctgccaag ctccccttcc tacacctggc acactgggt ctgcacaagg     2197
ctttgtcaac caaagacagc ttccccctttt tgattgcctg tagactttgg agccaagaaa   2257
cactctgtgt gactctacac acacttcagg tggtttgtgc ttcaaagtca ttgatgcaac    2317
ttgaaaggaa acagtttaat ggtggaaatg aactaccatt tataacttct gtttttttat    2377
tgagaaaatg attcacgaat tccaaatcag attgccagga agaaatagga cgtgacggta    2437
ctgggccctg tgattctccc agcccttgca gtccgctagg tgagaggaaa agctctttac    2497
ttccgccccct ggcagggact tctgggttat gggagaaacc agagatggga atgaggaaaa   2557
tatgaactac agcagaagcc cctgggcagc tgtgatggag cccctgacat tactcttctt    2617
gcatctgtcc tgccttcttt ccctctgcga ggcagtgggg tgggattcag agtgcttagt    2677
ctgctcactg ggagaagaag agttcctgcg catgcaagcc ctgctgtgtg gctgtcgttt    2737
acatttggga ggtgtcctgt atgtctgtac gttgggact gcctgtattt ggaagattta    2797
aaaacctagc atcctgttct caccctctaa gctgcattga gaaatgactc gtctctgtat    2857
ttgtattaag ccttaacact tttcttaagt gcattcggtg ccaacatttt ttagagctgt    2917
accaaaacaa aaagcctgta ctcacatcac aatgtcattt tgataggagc gttttgttat    2977
ttttacaagg cagaatgggg tgtaacagtt gaattaaact agcaatcacg tgctcagagc    3037
ttt                                                                  3040
```

<210> SEQ ID NO 2
<211> LENGTH: 190
<212> TYPE: PRT
<213> ORGANISM: Homo sapiens

<400> SEQUENCE: 2

```
Met Phe Gln Val Pro Asp Ser Glu Gly Gly Arg Ala Gly Ser Arg Ala
1               5                   10                  15

Met Lys Pro Pro Gly Gly Glu Ser Ser Asn Leu Phe Gly Ser Pro Glu
            20                  25                  30

Glu Ala Thr Pro Ser Ser Arg Pro Asn Arg Met Ala Ser Asn Ile Phe
        35                  40                  45

Gly Pro Thr Glu Glu Pro Gln Asn Ile Pro Lys Arg Thr Asn Pro Pro
    50                  55                  60

Gly Gly Lys Gly Ser Gly Ile Phe Asp Glu Ser Thr Pro Val Gln Thr
65                  70                  75                  80

Arg Gln His Leu Asn Pro Pro Gly Gly Lys Thr Ser Asp Ile Phe Gly
                85                  90                  95
```

Ser Pro Val Thr Ala Thr Ser Arg Leu Ala His Pro Asn Lys Pro Lys
            100                 105                 110

Asp His Val Phe Leu Cys Glu Gly Glu Pro Lys Ser Asp Leu Lys
        115                 120                 125

Ala Ala Arg Ser Ile Pro Ala Gly Ala Glu Pro Gly Glu Lys Gly Ser
    130                 135                 140

Ala Arg Lys Ala Gly Pro Ala Lys Glu Gln Glu Pro Met Pro Thr Val
145                 150                 155                 160

Asp Ser His Glu Pro Arg Leu Gly Pro Arg Pro Arg Ser His Asn Lys
                165                 170                 175

Val Leu Asn Pro Pro Gly Gly Lys Ser Ser Ile Ser Phe Tyr
            180                 185                 190

<210> SEQ ID NO 3
<211> LENGTH: 20
<212> TYPE: DNA
<213> ORGANISM: Homo sapiens

<400> SEQUENCE: 3
accacagtcc atgccatcac                                                20

<210> SEQ ID NO 4
<211> LENGTH: 20
<212> TYPE: DNA
<213> ORGANISM: Homo sapiens

<400> SEQUENCE: 4
tccaccaccc tgttgctgta                                                20

<210> SEQ ID NO 5
<211> LENGTH: 21
<212> TYPE: DNA
<213> ORGANISM: Homo sapiens

<400> SEQUENCE: 5
ccaacagaag aacctcagaa c                                              21

<210> SEQ ID NO 6
<211> LENGTH: 21
<212> TYPE: DNA
<213> ORGANISM: Homo sapiens

<400> SEQUENCE: 6
ctccttgcag ctttaagatc c                                              21

<210> SEQ ID NO 7
<211> LENGTH: 20
<212> TYPE: DNA
<213> ORGANISM: Homo sapiens

<400> SEQUENCE: 7
atgttccagg tcccggatag                                                20

<210> SEQ ID NO 8
<211> LENGTH: 20
<212> TYPE: DNA
<213> ORGANISM: Homo sapiens

<400> SEQUENCE: 8
ttagtagaag gagatgctgg                                                20

```
<210> SEQ ID NO 9
<211> LENGTH: 64
<212> TYPE: DNA
<213> ORGANISM: Homo sapiens

<400> SEQUENCE: 9
gatccccgga ggagaatcga gcaatctttt caagagaaag attgctcgat tctcctcctt      60
ttta                                                                  64

<210> SEQ ID NO 10
<211> LENGTH: 64
<212> TYPE: DNA
<213> ORGANISM: Homo sapiens

<400> SEQUENCE: 10
agcttaaaaa ggaggagaat cgagcaatct ttctcttgaa aagattgctc gattctcctc      60
cggg                                                                  64
```